United States Patent [19]

Pfaendler

[11] Patent Number: 4,683,303
[45] Date of Patent: Jul. 28, 1987

[54] REDUCTION PROCESS FOR THE PREPARATION OF 4-UNSUBSTITUTED AZETIDIN-2-ONES

[76] Inventor: Hans R. Pfaendler, Pippinplatz 1, D-8000 Munich 71, Fed. Rep. of Germany

[21] Appl. No.: 666,443

[22] Filed: Oct. 30, 1984

[30] Foreign Application Priority Data

Nov. 4, 1983 [DE] Fed. Rep. of Germany ....... 3340006

[51] Int. Cl.$^4$ .................... C07D 205/08; C07B 41/08
[52] U.S. Cl. .................................. 540/362; 540/363; 540/357
[58] Field of Search ................... 260/239 A; 540/362, 540/363

[56] References Cited

FOREIGN PATENT DOCUMENTS 0021678 6/1980 European Pat. Off. .
0078026 10/1982 European Pat. Off. .
1945542 9/1969 Fed. Rep. of Germany .

OTHER PUBLICATIONS

Brown et al., Tetrahedron 35, 567, (1979).
Rompps Chemie—Lexikon, Franckh'sche Verlagshandlung (Stuttgart), 8th Ed., p. 7.
Angewandte Chemie, vol. 74, p. 523, Lactame, Polymerisation und Verwendung Als Faserrohstoffe; Aug. 7, 1962; Graf, Lohaus et al.
Liebig's Ann. Chemie, vol. 614, (1968), p. 158, by Testa, Fontanella, et al.
Holley, J.A.C.S. 71, 2129, June 1949.
Allan and Morgan, "Action of Mesitylmagnesium Bromide etc.", Chemistry & Industry, Jul. 19, 1975, p. 614.
Suarato, Lombardi, et al., Tetrahedron Letters, 1978, p. 4059.
Birkofer, Schramm; Ann. Chem., 1975, 2195.
Searles & Wann; Chem & Industry, 1964, p. 2097., 12/19/64.
Testa, Fontanella et al; Helv. Chim. Acta 42, 2370.
Testa, Fontanella et al.; Disubstituierte Azetidine Ann. Chem. 626, 114, (1959).

Primary Examiner—Mark L. Berch

[57] ABSTRACT

Novel process for the preparation of azetidin-2-ones of the formula

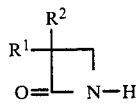

wherein $R^1$ and $R^2$ independently from each other are hydrogen, or an organic group linked to the ring carbon via a carbon atom, a nitrogen atom or an oxygen atom, characterized in that a corresponding 4-acyloxyazetidin-2-one, which is substituted by a group —O—CO—$R^3$ at the 4-position, wherein $R^3$ is hydrogen or an organic radical stable at the reaction conditions, is reacted with a complex metal hydride comprising reactive hydride ions, such as, lithium borohydride, sodium borohydride, potassium borohydride, zinc borohydride or tetraorganoammonium borohydride.

10 Claims, No Drawings

REDUCTION PROCESS FOR THE PREPARATION OF 4-UNSUBSTITUTED AZETIDIN-2-ONES

The present invention relates to a novel process for the preparation of azetidin-2-ones of the general formula I

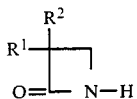

in which $R^1$ and $R^2$ independently from each other are hydrogen or an organic group linked to the ring carbon atom via a carbon, a nitrogen or an oxygen atom, with the proviso that $R^1$ and $R^2$ can not be an organic group linked via a carbonyl group to the ring carbon atom when one of the groups $R^1$ or $R^2$ is hydrogen.

Azetidin-2-one and consequently also the azetidin-2-ones of general formula I above are interesting compounds as such, but also important starting materials for the preparation for example of plastics for the production of synthetic fibers, for example of pharmaceuticals which for example act on the central nervous system or are antibiotics such as monocyclic β-lactams (monobactams).

From the 3-monosubstituted azetidin-2-ones and from the simplest unsubstituted azetidin-2-one (propiolactam) itself synthetic polypeptides can be manufactured for example (Angew. Chem. 74, p. 523 (1962), Ann. 614, p. 158 (1968), J. Am. Chem. Soc. 71, p. 2129 (1949), Chem. Ind. 1975, p. 614, and Ann. 1975 p. 2195)).

Certain 3,3'-disubstituted azetidin-2-ones are strong sedatives and hypnotics acting on the central nervous system (Ann. 614, p. 158 (1958)).

For the preparation of azetidinones including azetidin-2-ones of the above mentioned general formula I there are several different methods, which are both total syntheses and partial syntheses.

Thus, a number of N-alkyl-β-lactams can be prepared by the reaction of a β-amino ester with a Grignard reagent for example. In an analogous manner, the unsubstituted parent β-lactam, namely azetidin-2-one (β-propiolactam), can be prepared by cyclisation of β-alanine ethyl ester using a Grignard reagent such as ethyl magnesium bromide. These total syntheses from the first sight seem to be very simple, they furnish the desired azetidin-2-ones only in relatively low yields, however. Moreover, the stereochemistry of the compounds to be prepared cannot be selectively directed using these procedures. Procedures of this kind are described for example in J. Am. Chem. Soc., 71, p. 2129 to 2131 (1949), Chemistry and Industry, p. 2097 (1964) or Chemistry and Industry, p. 614 to 615 (1975).

The partial syntheses for the preparation of azetidin-2-ones practically exclusively start from compounds possessing the nucleus of the penicillins, namely from the penicillins, penicillanic acid, 6-aminopenicillanic acid or their esters. Thus, these starting materials are mono- or disubstituted at the 6-position of the nucleus. The substituents can either be desired for the relevant azetidin-2-one to be prepared or they can be removed during the production of the desired azetidin-2-one and/or they can be converted to other desired substituents by separate reactions. The carboxyl group at the 3-position of the nucleus of the starting materials can be free or esterified or protected else. By such partial syntheses azetidin-2-ones can be prepared which are either unsubstituted or mono- or disubstituted by various substituents at the 3-position. The positions 1 and 4 of these azetidin-2-ones are normally unsubstituted or bear substituents arising from the preparation of these compounds through the required ring opening process.

A partial synthesis as mentioned above is for example described in EP-OS 0 021 678, where it is specially referred to the reaction scheme on page 24 as well as to the corresponding description on pages 27 to 32. A further process of this kind is for example described in Tetrahedron Letters, p. 4059 to 4061 (1978). These processes follow generally the following reaction sequence, wherein (A) is defined as the first mentioned process and (B) is defined as the second mentioned process.

Reaction Scheme

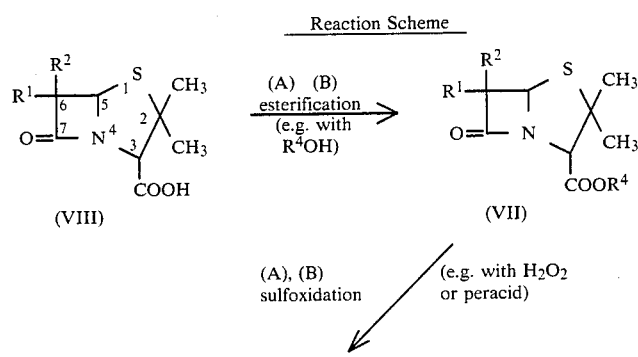

-continued
Reaction Scheme
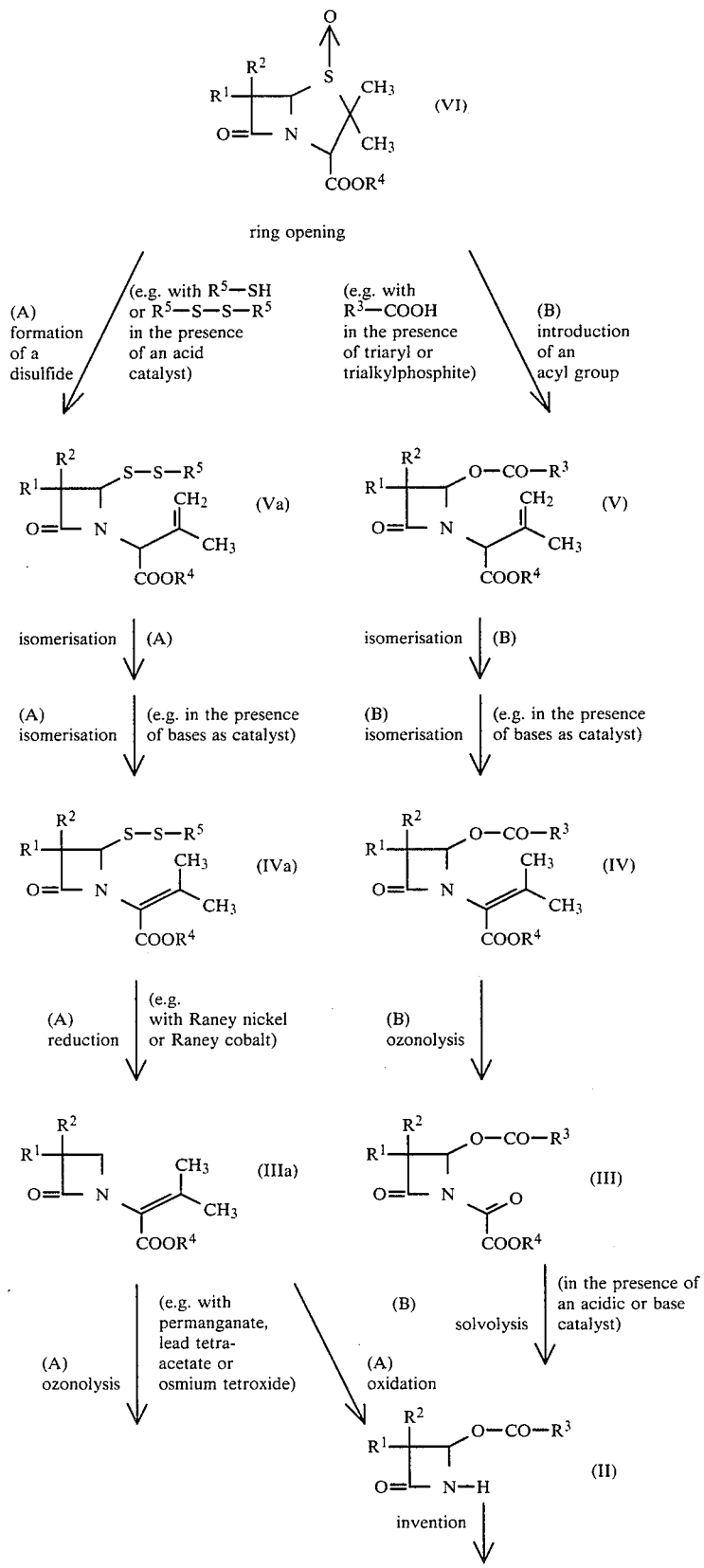

Reaction Scheme

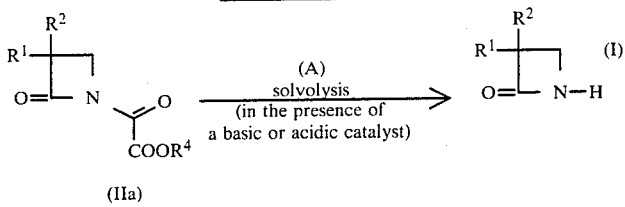

The partial syntheses for the preparation of azetidin-2-ones based on the penicillin nucleus and therefore also the partial syntheses for the preparation of azetidin-2-ones of the formula I are especially advantageous compared to the total syntheses, because the natural configuration and chirality of the starting materials usually are retained with the desired corresponding azetidin-2-one final products. These processes are not fully satisfactory unfortunately, either because they furnish the desired 4-unsubstituted azetidin-2-ones only in low yield (process A above), or because they are limited to the preparation of azetidin-2-ones possessing an acyloxy substituent at the 4-position (process B above) which are by conventional methods not convertible to the corresponding 4-unsubstituted azetidin-2-ones. A special bottle neck with unsatisfactory yields of process (A) arises by the reductive cleavage of the disulfide side chain at the 4-position using Raney nickel or Raney cobalt. Here, an approximately 300-fold excess of metal catalyst is required, and the yield to the desired product is nevertheless only about 20 to 30%. This means that for the preparation of one mole equivalent, i.e. 85 g of compound I, wherein $R^1$ is $NH_2$ and $R^2$ is hydrogen, 15 l (about 60 kg) of Raney nickel is required. In process (B) the bottle neck arises by the difficulty, that until now there was no known method allowing the cleavage of the 4-substituent without further modification of the structure of such an azetidin-2-one and furnishing the desired 4-unsubstituted azetidin-2-one in high yield.

In consequence of the mentioned disadvantages of the known processes for the preparation of azetidin-2-ones which are unsubstituted at the 4-position and also unsubstituted at the nitrogen in position 1 it is therefore the object of this invention to provide a new process for the preparation of azetidin-2-ones of the general formula I furnishing these compounds simply and in high yield and especially improving the above mentioned process (B) by a simple and elegant final step involving the cleavage of the 4-acyloxy side chain.

These objects are now obtained in the initially mentioned process of the invention in that a 4-acyloxy-azetidin-2-one of the general formula II

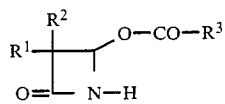

wherein $R^1$ and $R^2$ are as defined above and $R^3$ is hydrogen or an organic group stable at the reaction conditions, is reacted with a complex metal hydride containing reactive hydride ions.

This reaction works very smoothly and with high yield. Thus an entire procedure for the preparation of azetidin-2-ones on an industrial scale is provided, which consists essentially of process variant (B) shown in the above mentioned reaction scheme and which as additional and decisive element contains the final step of the cleavage of the acyloxy group in position 4. It is very surprising that this cleavage is effectuated by a metal hydride comprising reactive hydride ions. Obviously such a reaction was not expected to be possible, and this follows for example from EP-OS 0 078 026. There, on page 9 compounds 19 and 20 are described possessing an acetoxy group at the 4-position and being either protected at the ring nitrogen in the 1-position by a group such as t-butyldimethylsilyl, or being unsubstituted. It is mentioned there also that these ketoacetate compounds can be reduced to the compounds 9 and 10 shown at the beginning of page 8 using common reducing agents such as sodium borohydride, lithium borohydride, aminoboranes or hydrogen and metal catalysts. However, it was not realized thereby that by this procedure the acetoxy group present at the 4-position can also be cleaved and substituted by hydrogen. This is also confirmed by DE-OS 19 45 542, according to which azetidin-2-ones being either unsubstituted or mono- or disubstituted by lower alkyl at the position 3, being unsubstituted at the ring nitrogen and being substituted at the 4-position by a formyloxy group or an aliphatic or an aromatic acyloxy group with up to 10 carbon atoms, are reacted with a nucleophilic reagent to afford the corresponding azetidin-2-ones bearing the substituted arising from the nucleophilic reagent. Here again one substituent is only exchanged by an other substituent, but there is no cleavage resulting in a substitution by hydrogen. Such a substitution of an acyloxy group present at the 4-position of the azetidin-2-ones of the above mentioned general formula II by simply hydrogen has not been described yet and the successful processing of the processes of the invention was unexpected for the above mentioned reasons. There was even a prejudice against the inventive solution which, consequently, has to be considered as a chemically extraordinary process, based on a considerable inventive activity. By this process the relevant azetidin-2-ones are prepared in extraordinarily high yields. Compared to the above mentioned process (A) the preparation of one mole equivalent of compound of formula I ($R^1 = NH_2$, $R^2 = H$) is achieved with only about 140 g metal hydride.

For the procedure of the invention practically all known complex metal hydrides comprising reactive hydride ions can be used. Examples for such metal hydrides are lithium borohydride, sodium borohydride, potassium borohydride, zinc borohydride, sodium cyanoborohydride, lithium tri-sec.-butylborohydride, sodium trimethoxyborohydride, lithium cyanoborohydride, calcium borohydride, lithium aluminum hydride, sodium aluminum hydride, lithium diethoxyaluminum hydride, lithium triethoxyaluminum hydride, lithium tri-tert.-butoxyaluminum hydride, lithium triethyl borohydride, magnesium aluminum hydride, sodium aluminum diethyl dihydride, sodium bis-(2-methoxyethoxy)-aluminium hydride, or also tetra-lower-alkylammonium borohydride such as tetraethylammonium borohydride or tetrabutylammonium borohydride.

As complex metal hydrides preferably hydrides selected from the metals lithium, sodium, potassium, magnesium, calcium, zinc, boron and/or aluminum are used. Lithium borohydride, sodium borohydride, potassium borohydride and zinc borohydride are especially preferred. Furthermore also the tetraorganoammonium borohydrides such as tetraethylammonium borohydride or tetrabutylammonium borohydride are preferred.

The process of the invention is commonly carried out in presence of a protic and/or an aprotic solvent as commonly used in similar processes or as used in the preparation of the various starting materials in the former reaction steps. Examples of solvents suitable in many cases are for example water, methanol, ethanol, isopropanol, ether, methylene chloride or tetrahydrofuran. The solvents can be used individually or as mixtures, whereby mixtures with water are preferred.

The process of the invention is carried out at temperatures which are common for such reactions whereby the upper temperature limit is determined practically only by the decomposition temperature of the 4-acyloxyacetidin-2-ones of the general formula II and that of the resulting azetidin-2-ones of the general formula I. Generally reaction temperatures between about $-70°$ C. and about $+120°$ C. are used. Temperatures between about $0°$ C. and about $+50°$ C. are preferred.

The pH-value of the reaction mixture is only important in view that the starting materials as well as the products are not decomposed at the pH of the reaction mixture. Most suitably the process of the invention is carried out at a pH value between about 2 and 9, because a number of starting materials and products are not stable in alkaline medium at a pH above approximately 9.

The mole ratio between the starting materials, i.e. the 4-acyloxyazetidin-2-ones of the general formula II, and the metal hydride required for the cleavage of the 4-acyloxy side chain can be largely varied with the process of the invention. Commonly mole ratios between 4-acyloxyazetidin-2-one of the formula II and metal hydride are 1:0.5 to 3, preferably 1:1 to 1.5.

The reaction mixture resulting from the process of the invention can be worked up in the usual way for the recovering of the desired azetidin-2-ones of the general formula I.

The starting materials required for the process of the invention, i.e. the 4-acyloxyazetidin-2-ones of the general formula II, are either known compounds or compounds which can be prepared according to processes known per se. The same is true for the preparation of the starting materials required for the production of 4-acyloxyazetidin-2-ones of the general formula II. Preferably these starting materials are prepared by reactions as shown in the above mentioned reaction scheme (process B) namely starting from penicillanic acid, 6-aminopenicillanic acid or corresponding penicillins of the general formula VIII.

The substituents $R^1$ and $R^2$ of the compounds of the general formula I obtainable by the process of the invention, of the starting materials of the general formula II and also of the further starting materials VIII to III outlined in the reaction scheme for process (B), can be, independently from each other, hydrogen or an organic radical bound to the ring carbon by a carbon, nitrogen or oxygen atom. The character of these radicals $R^1$ and $R^2$ is practically irrelevant to the proceeding of the process of the invention. They can be hydrogen or any organic residues which are stable along the reaction sequence leading to the 4-acyloxyazetidin-2-ones of the general formula II and which are also stable in the process of the invention leading to azetidin-2-ones of the general formula I or which are optionally cleaved and substituted by hydrogen, substituted by other organic radicals or modified else during the various reactions.

The same is true for the radical $R^3$ in the 4-acyloxy group of the 4-acyloxyazetidin-2-ones of the general formula II. Consequently this radical can be hydrogen or any organic radical stable at the reaction conditions. When 4-acyloxyazetidin-2-ones of the general formula II are used for the process of the invention which have been prepared according to process (B) in the above mentioned reaction scheme, the radical $R^3$ is of course the organic radical of the carboxylic acid used for the ring opening reaction with a triaryl phosphite or a trialkyl phosphite. It is then incorporated as an acyloxy radical at position 4 into the compound of the general formula V obtained by a ring opening reaction. In certain cases the organic radical $R^3$ at the 4-position of the 4-acyloxyazetidin-2-ones of the general formula II and of the various other starting materials can be an organic radical which is unstable at the reaction conditions and which is altered under the influence of the metal hydride when the process of the invention is carried out. Thereby it is essential that the course of reaction is not affected by such a radical $R^3$, i.e. the desired cleavage of the acyloxy group at the position 4 by substitution by hydrogen is not affected.

The process of the invention is carried out preferably by using compounds of formula II, wherein $R^1$ and $R^2$ are, independently from each other, hydrogen, alkyl with 1 to 7 carbon atoms or alkoxy with 1 to 7 carbon atoms and $R^3$ is hydrogen or alkyl with 1 to 7 carbon atoms. Furthermore compounds of formula II are preferably used, wherein $R^1$ is an amino group or a protected amino group, $R^2$ is hydrogen, alkyl with 1 to 7 carbon atoms or alkoxy with 1 to 7 carbon atoms, and $R^3$ is hydrogen or alkyl with 1 to 7 carbon atoms. Preferred with both above mentioned possibilities is the use of compounds of formula I, wherein one of the radicals $R^1$ and $R^2$ is hydrogen. If $R^1$ is a protected amino group then its protecting group represents a common hydrocarbon oxycarbonyl group or a hydrocarbon carbonyl group. Especially preferred is the use of compounds of the formula II, wherein $R^1$ is a protected amino group, protected by phenylacetyl, phenoxyacetyl, benzyloxycarbonyl or tert.-butyloxycarbonyl, whereby the last two are very specially preferred, because with them special advantages arise within the former reaction steps. Naturally, for the preparation of azetidin-2-on itself starting materials of formula II are used, wherein $R^1$ and $R^2$ are both hydrogen. Especially preferred is the compound of formula II, wherein $R^3$ is methyl. Furthermore the use of compounds of the formula II is preferred wherein one of the substituents $R^1$ and $R^2$ is hydrogen and the other one is methyl or ethyl or wherein both of the substituents $R^1$ and $R^2$ are methyl or ethyl. If $R^1$ is a protected amino group which is preferably protected by phenoxyacetyl, benzyloxycarbonyl or tert.-butyloxycarbonyl, $R^2$ is preferably hydrogen or methyl, ethyl, methoxy or ethoxy. Within the preferred preparation of the 4-acyloxyazetidin-2-ones of the general formula II, starting from the nucleus of the penicillins, the ring opening reaction proceeds preferably in presence of acetic acid. Thus, compounds of the above described kind are preferred, wherein $R^3$ is methyl.

The substituent $R^4$ within the two processes (A) and (B) as shown in the formerly mentioned reaction scheme, can be also any stable organic residue, naturally. This residue arises from the alcohol used in the esterification of the penicillin carboxyl group. Thus substituent $R^4$ can be any residue of any common carboxyl protection group. Also $R^5$, present in the variant (B) of the above shown reaction sequence can be any organic residue arising from the thiol or disulfide involved in the ring opening reaction.

As, according to the above mentioned explanations the radicals $R^1$ and $R^2$ are not directly involved in the process of the invention and do not affect this reaction they can be, independently from each other, hydrogen or any organic radical bound by a carbon, nitrogen or oxygen atom to the ring carbon atom. These radicals, bound by the mentioned atoms to the ring carbon atom can be any saturated or unsaturated, optionally substituted aliphatic, aromatic or araliphatic hydrocarbon radicals with up to 18 carbon atoms, preferably up to 10 carbon atoms, and especially up to 7 carbon atoms. They can be further also heterocyclyl or heterocyclyl-loweralkyl radicals with up to 10 carbon atoms and up to 4 ring heteroatoms selected from nitrogen, oxygen and/or sulfur. Furthermore $R^1$ and $R^2$ can also be functionalized carboxy, for example, optionally substituted lower alkyl or lower alkenyl or optionally substituted cycloalkyl, cycloalkenyl, cycloalkyl-loweralkyl, cycloalkyl-loweralkenyl, phenyl, phenyl-loweralkyl or phenyl-loweralkenyl.

The loweralkyl radicals (or also the loweralkoxy radicals bound by an oxygen atom to the ring carbon atom) preferably contain up to 7 carbon atoms, especially up to 4 carbon atoms and examples thereof are methyl, ethyl, propyl, isopropyl, butyl, tert-butyl or pentyl. Substituted lower alkyl radicals are primarily substituted methyl, ethyl or propyl, whereby the substituents are mainly located at the 1-position, but can also be located at the 2 or 3-positions. Such substituted lower alkyl radicals are, for example, hydroxyloweralkyl, such as hydroxymethyl, hydroxyethyl or hydroxypropyl, loweralkoxyloweralkyl, such as loweralkoxymethyl, loweralkoxyethyl or loweralkoxypropyl, for example methoxymethyl, methoxyethyl or methoxypropyl, loweralkanoyloxyloweralkyl, such as loweralkanoyloxymethyl, loweralkanoyloxyethyl or loweralkanoyloxypropyl, for example acetoxymethyl, propionoyloxymethyl, acetyloxyethyl, acetyloxypropyl, in its salt form such as a sodium salt or ammonium salt existing hydroxysulfonyloxyloweralkyl such as hydroxysulfonyloxymethyl, hydroxysulfonyloxyethyl, hydroxysulfonyloxypropyl, halogenated loweralkyl such as halogenated methyl, halogenated ethyl or halogenated propyl, for example chloroethyl, bromoethyl, chloropropenyl or bromopropenyl, loweralkylthioloweralkyl such as methylthiomethyl, methylthioethyl, methylthiopropyl or tert.butylthiomethyl, loweralkoxycarbonylloweralkyl, such as loweralkoxycarbonylmethyl or loweralkoxycarbonylethyl, for example methoxycarbonylmethyl, methoxycarbonylethyl, ethoxycarbonylmethyl, or ethoxycarbonylethyl, cyanoloweralkyl, such as cyanomethyl or cyanoethyl, sulfoloweralkyl, such as sulfomethyl, sulfoethyl or sulfopropyl, wherein the sulfo group exists in its salt form, for example as a alkali salt, such as the sodium salt, or also as an ammonium salt, or in certain cases is protected, for example also can be acylated aminoloweralkyl, such as aminomethyl, aminoethyl or aminopropyl. When the substituents $R^1$ and/or $R^2$ are loweralkyl radicals, then they contain preferably 2 to 7 carbon atoms, especially 2 to 4 carbon atoms and examples thereof are vinyl, allyl, 2-butenyl or 3-butenyl. The loweralkyl radicals can also be substituted, whereby they can be substituted by the same substituents as defined above in connection with the substituents of the loweralkyl radicals.

An optionally modified carboxyl group is a free, esterified or amidated carboxyl group, for example loweralkoxycarbonyl, such as methoxycarbonyl, ethoxycarbonyl or tert.-butoxycarbonyl, arylloweralkoxycarbonyl, such as benzyloxycarbonyl, p-loweralkylbenzyloxycarbonyl or diphenylmethoxycarbonyl, aryloxycarbonyl, for example optionally substituted phenyloxycarbonyl, the substituents of which are halogen, such as chlorine, or loweralkoxy, such as methoxy, or nitro. Examples are phenyloxycarbonyl itself, o-, m-, or p-chlorophenyloxycarbonyl, pentachlorophenyloxycarbonyl, o-, m-, or p-methoxyphenyloxycarbonyl or p-nitrophenyloxycarbonyl or aminocarbonyl, which also can be mono- or disubstituted, for example by lower alkyl such as methyl or or ethyl.

If $R^1$ and/or $R^2$ are cycloalkyl radical, it can contain for example, 3 to 7 carbon atoms such as cyclopropyl, cyclobutyl, cyclopentyl or hyclohexyl. A cycloloweralkyl radical, for example, can contain 4 to 7 carbon atoms, such as cyclopropylmethyl, cyclobutylmethyl, cyclopentylmethyl or cyclohexylmethyl.

If $R^1$ and/or $R^2$ are a cycloalkenyl radical, it can also contain 3 to 7 carbon atoms and contain one or two double bonds and examples thereof are cyclohexenyl, such as 1-cyclohexenyl, or cyclohexadienyl, such as 1,4-cyclohexadienyl.

As cycloloweralkylloweralkenyl radicals or cycloalkenylloweralkyl radicals for example cyclohexylvinyl, cyclohexylallyl, cyclohexylmethyl or 1,4-cyclohexadienylmethyl are suitable.

If $R^1$ and/or $R^2$ are a phenyl radical, a phenylloweralkyl radical or a phenylloweralkenyl radical, these radicals can also be substituted at the lower alkyl group as well as at the nucleus and examples for such radicals are benzyl or 1- or 2-phenylethyl, whereby the substituents can be lower alkyl such as methyl or ethyl, lower alkoxy, such as methoxy, or halogen, such as fluorine or chlorine. Furthermore the substituents can also be nitro or amino. A phenylloweralkyl can for example also be substituted at the α-position and such substituients are for example hydroxy, hydroxysulfonyloxy, carboxy, sulfo or amino.

If $R^1$ and/or $R^2$ is an optionally substituted heterocyclyl or heterocyclylloweerealkyl radical, then the heterocycle is bound by a carbon atom and preferably possesses aromatic character and examples thereof are pyridyl, such as 2-, 3-, or 4-pyridyl, thienyl, such as 2-thienyl or furyl, such as 2-furyl, or pyridylloweralkyl, thienylloweralkyl, or furylloweralkyl, whereby loweralkyl preferably is methyl. such heterocyclylloweralkyl radicals can also be substituted at the α-position, and examples for these substituents are again hydroxy, hydroxysulfonyloxy, carboxy, sulfo or amino.

As heterocyclylloweralkenyl radicals the same radicals as described above are defined, and examples thereof are phenylvinyl or furylallyl.

In certain cases $R^1$ and/or $R^2$ can also be a naphthyl radical, a naphthylloweralkyl radical or a naphthylloweralkenyl radical, whereby such radicals can be optionally substituted by substituents of the above mentioned kind.

Substituents or functionally modified substituents are optionally etherified or esterified hydoxy groups or mercapto groups, such as hydroxy itself, lower alkoxy, such as methoxy or ethoxy, lower alkanoyloxy, such as acetyloxy or propionoyloxy, hydroxysulfonyloxy, halogen, such as chlorine or bromine, or loweralkylmercapto, such as methylthio are possible, whereby a functionally modified carboxy group includes for example carboxy itself, loweralkoxycarbonyl, such as methoxycarbonyl or ethoxycarbonyl, carbamoyl or cyano, furthermore also nitro, sulfo or optionally mono- or disubstituted amino, whereby the substituents can for example include loweralkyl, such as methyl or ethyl, loweralkanoyl, such as acetyl, or lower alkylen, such as 1,4-butylen, or 1,5-pentylen.

Corresponding definitions as described for the radicals $R^1$ and $R^2$ are generally also true for radical $R^3$ as inter alia contained in general formula II.

The substituients $R^2$ and/or $R^3$ can be, as already mentioned, also amino, which optionally is protected. Here all the protecting groups applied in peptide chemistry for the protection of amino acids are included. Examples are acyl groups.

If, for example $R^1$ and/or $R^2$ are acylamino, the acyl residue can be any acyl group, present in the natural or synthetic penicillins and cephalosporins. Such acyl groups within the natural penicillins and cephalosporins are for example phenylacetyl or phenoxyacetyl.

Examples for acyl groups which can be included in the radicals $R^1$ and/or $R^2$, when these are acylamino, are the following:

(a) Groups of the general formula

wherein $R_a$ is lower alkyl or an optionally substituted heterocyclic group, (b) groups of the general formula

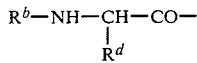

wherein $R^b$ is hydrogen, an optionally substituted amino acid residue, an amino-protecting group, a group of the formula $$R^c-(CH_2)_n-CO-,$$

wherein $R^c$ is an optionally substituted heterocyclic group, optionally substituted phenyl, optionally substituted lower alkyl, optionally substituted phenylthio or lower alkylthio, n is an integer of 0 to 4, the group $-(CH_2)_n-$ may optionally be substituted, a group of the general formula

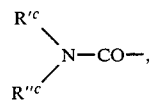

wherein $R'^c$ and $R''^c$ may be the same or different, and are hydrogen, lower alkyl, lower alkylcarbamoyl, optionally substituted phenylcarbonyl or sulfo, or a group of the general formula

wherein
$R'''^c$ is optionally substituted lower alkyl, and
$R^d$ is hydrogen, an optionally substituted lower alkyl, optionally substituted phenyl, optionally substituted heterocyclic group, cycloalkylene or optionally substituted heterocyclo-carbonylamino in which an alkylene chain may stand between the heterocyclic and carbonylamino moieties;

(c) groups of the general formula

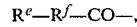

wherein $R^e$ is a group of the general formula

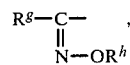

wherein $R^g$ is an optionally substituted heterocyclic group or optionally substituted phenyl, and $R^h$ is hydrogen, an optionally substituted lower acyl group, lower alkyl or a group of the general formula

wherein $R^j$ is carboxyl, an ester group or a heterocyclic group and $R^i$ is lower alkylene or lower alkenylene, and $R^f$ is a single bond or a group of the general formula

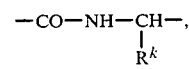

wherein $R^k$ is lower alkyl, optionally substituted phenyl or optionally substituted heterocyclic group, (d) groups of the general formula

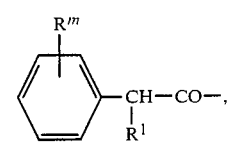

wherein $R^l$ is hydroxy, sulfoxy, carboxyl, optionally substituted sulfamoyl, sulfo, optionally substituted phenoxycarbonyl, benzyloxycarbonyl or formyloxy and $R^m$ is hydrogen, a lower alkyl group, a lower alkoxy group, halogen or hydroxy and (e) groups of the general formula

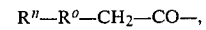

wherein $R^n$ is cyano, optionally substituted phenyl, optionally substituted phenoxy, lower alkyl, alkenylene or optionally substituted heterocyclic group and $R^o$ is a single bond or sulfur.

Examples for lower alkyl groups $R^a$ are methyl, ethyl, propyl, butyl or pentyl. The heterocyclic moiety of the optionally substituted heterocyclic group $R^a$ is a 5- or 6-membered heterocyclic group containing 1 or 2 nitrogen atoms which may optionally also contain a single oxygen or sulfur atom. Examples of such heterocyclic groups are isoxazolyl, piperazinyl or imidazolinyl. The substituents on such heterocyclic groups may, for example, be lower alkyl or 1 to 3 carbon atoms, lower alkoxy of 1 to 3 carbon atoms, halogen, nitro, amino, oxo, thioxo and optionally substituted phenyl. The substituents of the optionally substituted phenyl group may include, for example, lower alkyl of 1 to 3 carbon atoms, lower alkoxy of 1 to 3 carbon atoms, halogen, nitro or amino.

Examples of the optionally substituted amino acid residue $R^b$ are glycyl, alanyl, valyl, leucyl, isoleucyl, seryl, threonyl, cysteinyl, crystyl, methionyl, α- or β-aspartyl, α- or β-glutamyl, lysyl, arginyl, phenylalanyl, phenylglycyl, tyrosyl, histidyl, tryptophyl or prolyl. The substituents on these optionally substituted amino acid residues may include, for example, amino, lower alkylamino, amino-protecting groups, carbamoyl, methylcarbamoyl, sulfamoyl, benzyl, 4-ethyl-2,3-dioxo-1-piperidinocarbonyl and 4-ethyl-2,3-dioxo-1-piperidinocarbonylamino. The lower alkyl moiety of the lower alkyl amino is preferably alkyl of 1 to 3 carbon atoms. The amino-protecting group may, for example, be one of the protective groups mentioned hereinafter for amino groups.

The optionally substituted heterocyclic group $R^d$ includes, for example, 5- or 6-membered heterocyclic groups containing a sulfur, nitrogen or oxygen atom, 5- or 6-membered heterocyclic goups containing 2 to 4 nitrogen atoms and 5- or 6-membered heterocyclic groups containing one or two nitrogen atoms and one sulfur or oxygen atom. These heterocyclic groups may each be fused to a 6-membered ring containing one or two nitrogen atoms, a benzene ring or a 5-membered ring which can also contain sulfur. As examples of the heterocyclic group $R^d$, there may be mentioned 2-pyridyl, 3-pyridyl, 4-pyridyl, pyrimidinyl, pyrazinyl, pyridazinyl, piperazinyl, pyrazolinyl, imidazolidinyl, thiazolyl, isothiazolyl, oxazolyl, isoxazolyl, pyrido)2,3-d)pyrimidinyl, benzopyranyl, 1,5-naphthyridinyl, 1,6-naphthyridinyl, 1,7-naphthyridinyl, 1,8-naphthyridinyl, 2,6-naphthyridinyl, 2,7-naphthyridinyl, quinolinyl, thieno(2,3-b)pyridinyl, tetrazolyl, thiadiazolyl, oxadiazolyl, triazinyl, thienyl, pyrolyl or furyl. The substituents of such optionally substituted heterocyclic groups $R^d$ include, for example, optionally substituted alkyl of 1 to 12 carbon atoms, hydroxy, oxo, thioxo, formyl, trifluoromethyl, amino, halogen, alkylsulfonyl of 1 to 3 carbon atoms, coumarin-3-carbonyl, 4-formyl-1-piperazinyl, pyrrolaldoimino, furanaldoimino, thiophenaldoimino, mesyl, amino-protecting groups, acylamino of 2 to 4 carbon atoms which may be substituted by halogen for example. The amino-protecting group may, for example, be one of the protective groups mentioned hereinafter for amino groups. The substituents on the optionally substituted alkyl of 1 o 12 carbon atoms include, for example, phenyl, halogen, hydroxy or dialkylamino. The alkyl moiety of the dialkylamino is preferably alkyl of 1 to 3 carbon atoms.

The substituents of the optionally substituted phenylthio group $R^d$ include, for example, lower alkyl of 1 to 3 carbon atoms, lower alkoxy of 1 to 3 carbon atoms, halogen, hydroxy or amino.

The substituents for the optionally substituted group —$(CH_2)_n$— include, for example, amino and the group of the formula —NH—COR''''$^c$, wherein R''''$^c$ is amino or optionally substituted piperazinyl. As examples of the optionally substituted piperazinyl group R''''$^c$ there may be mentioned lower alkyl of 1 to 3 carbon atoms, lower alkoxy of 1 to 3 carbon atoms, hydroxy, oxo, thioxo and halogen.

Referring to the above formula, the lower alkyl represented by R'$^c$ and/or R''''$^c$ is preferably a group of 1 to 3 carbon atoms. The lower alkyl moiety of the lower alkylcarbamoyl is preferably a group of 1 to 3 carbon atoms.

As examples of the substituents on the optionally substituted phenylcarbonyl group, there may be mentioned lower alkyl of 1 to 3 carbon atoms, halogen, hydroxy, sulfoxy or benzyloxy.

The lower alkyl moiety of the optionally substituted lower alkyl group R'''$^c$ in the general formula

$$R'''^c-SO_2-$$

is preferably a moiety of 1 to 6 carbon atoms, which may be substituted by one or two substituents such as amino, carboxy, benzyloxycarbonyl or protected amino. The protective group in the protected amino may, for example, be one of the protective groups mentioned hereinafter for amino groups.

The lower alkyl moiety of the optionally substituted lower alkyl group $R^d$ is preferably a moiety of 1 to 3 carbon atoms. As examples of the substituent on the optionally substituted lower alkyl groups, there may be mentioned phenyl, carbamoyl, methylcarbamoyl, methylthio, thienylacetamido, ethoxycarbonylmethylcarbamoyl, N-methyltetrazolylthio, halogen and sulfamoyl. The substituents on the optionally substituted phenyl groups $R^d$ include, for example, lower alkyl of 1 to 3 carbon atoms, lower alkoxy of 1 to 3 carbon atoms, halogen, hydroxy, sulfoxy, benzyloxy, benzoyloxy, trimethylsilyl or acyloxy of 2 to 10 carbon atoms. The heterocyclic ring on the optionally substituted heterocyclic group $R^d$ may, for example, be a five-membered heterocyclic group with one or two nitrogen atoms and one sulfur or oxygen atom, or a five or six-membered heterocyclic group with 2 to 4 nitrogen atoms. Examples of such heterocyclic groups are thiazolyl, isothiazolyl, oxazolyl, isoxazolyl, thienyl, furyl, pyrrolyl, imodazolyl, pyrazinyl, pyrimidinyl, pyridazinyl, piperazinyl, triazinyl, tetrazolyl, thiadiazolyl or oxidiazolyl. such heterocyclic groups can optionally be substituted by lower alkyl of 1 to 3 carbon atoms, lower alkoxy of 1 to 3 carbon atoms, halogen, hydroxy, nitro, sulfoxy, amino and acylamino of 2 to 4 carbon atoms, and these substituents may be optionally substituted by halogen, for example.

The cycloalkylene $R^d$ is preferably a five- or six-membered cycloalkenylene, such as cyclohexenyl or cyclohexadienyl. The heterocyclic moiety of the optionally substituted heterocyclic carbonylamide which may optionally have an alkylene chain between the heterocyclic and the carbonylamino group represented by $R^d$ includes, for example, a six-membered heterocyclic group with two nitrogen atoms. Among such heterocyclic groups is piperazinyl. The substituents may for example be alkyl of 1 to 12 carbon atoms, lower alkoxy of 1 to 3 carbon atoms, oxo, thioxo or amino. The alkylene chain is preferably an alkylene chain of 1 to 3 carbon atoms and as examples for this chain are methylene, ethylene and n-propylene.

In formula

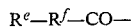

$$R^e-R^f-CO-$$

mentioned under section (c) above, the heterocyclic group can be, provideed $R^e$ is $R^g$, for example a 5-membered heterocyclic group containing a sulfur, nitrogen or oxygen atom and such heterocyclic groups have the above shown formula

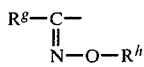

Examples of such heterocyclic groups are 2-thiazolyl, 4-thiazolyl, 5-thiazolyl, 2-thienyl, 3-thienyl, 2-furyl, 3-furyl, 2-pyrrolyl or 3-pyrrolyl. The substituents on such heterocyclic groups include, for example, lower alkyl of 1 to 3 carbon atoms, lower alkoxy of 1 to 3 carbon atoms, hydroxy, halogen, amino and acylamino groups of 2 to 4 carbon atoms and such substituents which may be optionally substituted by halogen, for example.

The substituents on the optionally substituted phenyl group $R^g$ include, for example, lower alkyl of 1 to 3 carbon atoms, lower alkoxy of 1 to 3 carbon atoms, halogen, nitro, amino, hydroxy and substituted hydroxy. The substituents of the substituted hydroxy may, for example, be benzyl, benzoyl, acyl of 2 to 10 carbon atoms, γ-D-glutamyl or 3-amino-3-carboxypropyl.

The lower alkyl group $R^h$ is preferably a group of 1 to 3 carbon atoms. The optionally substituted lower acyl group $R^h$ can be substituted by halogen, for example. The lower alkylene $R^i$ in the group —$R^i$—$R^j$— of the group $R^h$ is preferably a group of 1 to 3 carbon atoms, such as methylene, ethylene, propylene or isopropylene, for example. The lower alkylene $R_i$ is preferably a group of 1 to 3 carbon atoms, such as vinylene or propylene, for example. The carboxyl ester $R^j$ may, for example, be methyl ester, ethyl ester, propyl ester. The heterocyclic group $R^j$ may, for example, be a six-membered heterocyclic group with one nitrogen and one oxygen atom, such as morpholino, for example.

The lower alkyl group $R^f$ in the above mentioned formula

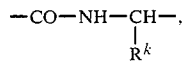

is preferably a group of 1 to 3 carbon atoms. As examples of substituents on optionally substituted phenyl groups $R^k$ there may be mentioned lower alkyl of 1 to 3 carbon atoms, halogen, nitro, amino or acyloxy of 2 to 10 carbon atoms, for example. The substituted heterocyclic group $R^k$ may, for example, be a five-membered heterocyclic group with one sulfur, nitrogen or oxygen atom, a five-membered heterocyclic group with one or two nitrogen atoms and one sulfur atom or oxygen atom and a five-membered heterocyclic group with two to four nitrogen atoms such as thiazolyl, isothiazolyl, oxazolyl, isoxazolyl, thienyl, furyl, pyrrolyl, thiadiazolyl, oxadiazolyl, triazinyl, tetrazinyl, tetrazolyl, imidazolyl, pyrazinyl, pyrimidinyl, pyridazinyl or piperazinyl. The substituents on the optionally substituted heterocyclic group include, for example, lower alkyl of 1 to 3 carbon atoms, lower alkoxy of 1 to 3 carbon atoms, halogen, hydroxy, amino, acylamino group of 1 to 3 carbon atoms which may be optionally substituted by halogen, for example.

Substituents on optionally substituted sulfamoyl groups $R^l$ include, for example, lower alkyl of 1 to 3 carbon atoms, or amidino, for example. Substituents on substituted phenoxycarbonyl groups $R_1$ include, for example, lower alkyl of 1 to 3 carbon atoms and lower alkoxy of a to 3 carbon atoms.

The lower alkyl or lower alkoxy $R^m$, mentioned in the formula of section (d) above are preferably groups of 1 to 3 carbon atoms. Substituents on substituted phenyl groups $R_n$ include, for example, lower alkyl of 1 to 3 carbon atoms, alkoxy with 1 to 3 carbon atoms, halogen, nitro, amino, hydroxy or optionally substituted aminomethyl. Substituents on the substituted aminomethyl may, for example, be carbamoyl, (2-oxo-3-benzylidenaminoimidazolidin-1-yl)carbonyl or (2-oxo-3-imidazolin-1-yl)carbonyl, for example. Substituents on the substituted phenoxy groups $R^n$, for example, include lower alkyl of 1 to 3 carbon atoms, lower alkoxy of 1 to 3 carbon atoms, halogen, nitro, amino, hydroxy or aminomethyl, for example. The optionally substituted lower alkyl group $R^n$ is preferably a group of 1 to 6 carbon atoms, the substituents being exemplified by halogen, hydroxy, cyano or trifluoromethyl.

The akylene of optionally substituted alkylene group $R^n$ may, for example, be vinylene or propylene and the substituents may for example be carboxyl or cyano. Examples of the heterocyclic ring of optionally substituted heterocyclic group $R^n$ include five- or six-membered heterocyclic groups including, for example, one sulfur atom or one to four nitrogen atoms and the five- or six-membered heterocycles including, for example, one sulfur atom and one nitrogen atom or one oxygen atom. Thus, 2-thienyl, 3-thienyl, 2-pyridyl, 3-pyridyl, 4-pyridyl, 2-thiazolyl, 4-thiazolyl, 5-thiazolyl, isothiazolyl, 1-tetrazolyl, 5-tetrazolyl, pyrrolidinyl, imidazolyl or 1,4-oxathiinyl, for example, may be mentioned. Substituents on such optionally substituted heterocyclic groups $R^n$ include, for example, lower alkyl of 1 to 3 carbon atoms, lower alkoxy of 1 to 3 carbon atoms, halogen, nitro, hydroxy, amino, carboxy, oxo, acylamino of 2 to 4 carbon atoms which may be optionally substituted by halogen or acyl of 2 to 4 carbon atoms, for example.

The alkyl group of 1 to 12 carbon atoms, mentioned hereinbefore, may for example be methyl, trifluoromethyl, ethyl, n-propyl, isopropyl, n-butyl, isobutyl, sec-butyl, tert-butyl, pentyl, isopentyl, hexyl, isohexyl, heptyl, octyl, nonyl, decyl, undecyl or dodecyl, for example.

The lower alkyl group of 1 to 6 carbon atoms mentioned hereinbefore, may for example be methyl, trifluoromethyl, ethyl, n-propyl, isopropyl, n-butyl, isobutyl, sec.-butyl, tert-butyl, pentyl, isopentyl, hexyl or isohexyl.

The lower alkyl groups of 1 to 3 carbon atoms, also mentioned hereinbefore, may for example be methyl, trifluoromethyl, ethyl, n-propyl or isopropyl.

The lower alkoxy groups with 1 to 3 carbon atoms, mentioned hereinbefore, may for example be methoxy, ethoxy, n-propoxy or isopropoxy.

The halogen includes chlorine, bromine, iodine and fluorine.

The lower alkylsulfonyl groups containing 1 to 3 carbon atoms include, for example, methylsulfonyl, ethysulfonyl, n-propylsulfonyl or isopropylsulfonyl.

The acylamino groups of 2 to 4 carbon atoms include, for example, acetylamino, propioylamino, n-butyrylamino or isobutyrylamino.

The acyloxy groups of 2 to 10 carbon atoms include, for example, acetoxy, n-propionyloxy, n-butyryloxy, isobutyryloxy, n-pentanoyloxy, n-hexanoyloxy, n-heptanoyloxy, n-octanoyloxy, n-nonanoyloxy or n-decanoyloxy.

Referring to the aforementioned acyl groups represented by by the general formula $R^a$—CO—, for example, the acyl groups include 3-(2,6-dichlorophenyl)-5-methylisoxazole-4-yl-carbonyl, 4-ethyl-2,3-dioxo-1-piperazinocarbonyl or 2-oxoimidazolidin-1-yl.

The acyl group represented by the formula

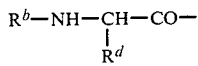

includes, for example, D-alanyl, D-phenylalanyl, α-benzyl-N-carbobenzoxy-γ-D-glutamyl-D-alanyl, N-carbobenzoxy-D-phenylglycyl, D-alanyl-D-phenylglycyl, γ-D-glutamyl-D-alanyl, N-carbobenzoxy-D-alanyl-D-phenylglycyl, D-carbamoylthryptophyl-D-phenylglycyl, methylaminoasparaginyl-D-phenylglycyl, N-carbobenzoxymethylamidoasparaginyl-D-phenylglycyl, N-carbobenzoxy-D-phenylglycyl-D-phenylglycyl, 2-(2,3-diaminopropionamido)-2-phenylacetyl, D-alanyl-D-alanyl, 2-(2-amino-3-(N-methylcarbamoyl)-propionamido)acetyl, 2-(2-amino-3-sulfamoylpropionamido)-2-phenylacetyl, 2-(2-amino-3-(4-ethyl-2,3-dioxo-1-piperazinocarboxamido)propionamido)-2-phenylacetyl, D-2-(4-ethyl-2,3-dioxo-1-piperazinocarboxamido)-2-(4-methoxyphenyl)acetyl, 4-ethyl-2,3-dioxo-1-piperazinocarbonyl, D-2-(2-(4-ethyl-2,3-dioxo-1-piperazinocarboxamido)-3-(N-methylcarbamoyl)propionamido)-2-phenylacetyl, D-2-(4-ethyl-2,3-dioxo-1-piperazinocarboxamido)acetamido)-2-phenylacetyl, D-2-(3-sulfamoyl-2-benzyloxycaboxamidopropionamido)-2-phenylacetyl, D-2-(2-benzyloxycarboxamido-3-(4-methoxyphenyloxycarboxamido)-propionamido)-2-phenylacetyl, 2-(2-benzyloxycarboxamido-3-(N-methylcarbamoyl)propionamido)acetyl, 2-(N-carbobenzoxy-D-phenylglycylamino)-3-(N-methylcarbamoyl)propionyl, N-carbobenzoxy-D-alanyl, 2-(benzyloxycarboxamido)-2-phenylacetyl, 2-(benzyloxycarboxamido-3-N-methylcarbamoylpropionyl, N-(4-ethyl-2,3-dithioxo-1-piperazinocarbonyl)-D-phenylglycyl, 2-(2-amino-4-thiazolyl) -2-(4-ethyl-2,3-(4-ethyl-2,3-dioxo-1-piperazinocarboxamido)acetyl, 2-(2-phenylacetamido)propionyl, 2-(4-ethyl-2,3-dioxo-1-piperazinocarboxamido)-2-thienylacetyl, 2-(3-furfurylidenamino-2-oxoimidazolidine-1-carboxamido)-2-(4-hydroxyphenyl)acetyl, 2-(8-hydroxy-1,5-naphthyridine-7-carboxamido)-2-phenylacetyl, 2-(4-n-octyl-2,3-dioxo-1-piperazinocarboxamido-2-phenylacetyl, 2-(4-ethyl-2,3-dioxo-1-piperazinocarboxamido)-2-(4-sulfoxylphenyl)acetyl, 2-(4-ethyl-2,3-dioxo-1-piperazinocarboxamido)-2-(4-chlorophenylacetyl, 2-(4-n-octyl-2,3-dioxo-1-piperazinocarboxamido)-2-(4-hydroxysulfonyloxyphenyl)acetyl, 2-(4ethyl-2,3-dioxo-1-piperazinocarboxamido)-2-(4-methoxyphenyl)acétyl, 2-(4-ethyl-2,3-dioxo-1-piperazinocarboxamido)-2-(4-trimethylsilylphenyl)acetyl, 2-(4-ethyl-2,3-dioxo-1-piperazinocarboxamido)-2-(3-chloro-4-methoxyphenyl)-acetyl, 2-(4-ethyl-2,3-dioxo-1-piperazinocarboxamido)-2-(3-chloro-4-hydroxysulfonyloxyphenyl)acetyl, 2-(4-ethyl-2,3-dioxo-1-piperazinocarbonyl)-2-(4-benzyloxyphenyl)acetyl, 2-(4-n-octyl-2,3-dioxo-1-piperazioncarboxamido)-2-(4-hyrdoxyphenyl)acetyl, N-(4-ethyl-2,3-dioxo-1-piperazinocarbonyl)glutaminyl, N-(4-ethyl-2,3-dioxo-1-piperacinocarbonyl)phenylalanyl, N-(4-ethyl-2,3-dioxo-1-piperazinocarbonyl)D-alanyl, 2-(4-ethyl-2,3-dioxo-1-piperazinocarboxamido-2-(4-hydroxyphenyl)acetyl, 2,2-bis(4-ethyl-2,3-dioxo-1-piperazinocarboxamido)acetyl, 2-(4-ethyl-2,3-dioxo-1-piperazinocarboxamido)-2-(1-cyclohexen-1-yl)acetyl, 2-(4-n-octyl-2,3-dioxo-1-piperazinocarboxamido)-2-thienylacetyl, 2-(4-ethyl-2,3-dioxo-1-piperazinocarboxamido)-2-(2-amino-4-thiazolyl)acetyl, 2-(4-ethyl-2,3-dioxo-1-piperazinocarboxamido)-2-(chloroacetamido-4-thiazolyl)acetyl, 2-(4-ethyl-2,3-dioxo-1-piperazinocarboxamido)-2-(2-methyl-4-thiazolyl) acetyl, 2-(4-ethyl-2,3-dioxo-1-piperazinocarboxamido)-2-(2-acetamido-4-thiazolyl)acetyl, 2-(4-n-octyl-2,3-dioxo-1-piperazinocarboxamido)-2-(2-amino-4-thiazolyl)acetyl, 2-(4-ethyl,2,3-dioxo-piperazinocarboxamido)-2-furylacetyl, 2-(4-ethyl,2,3-dioxo-1-piperazinocarboxamido)-2-(2-pyrrolyl)acetyl, 2-(4-ethyl-2,3-dithioxo-1-piperazinocarboxamido) 2-(4-hydroxyphenyl)acetyl, 2-(4-n-octyl-2,3-dioxo-1-piperazinocarboxamido)-2-(2-chloroacetamido-4-thiazolyl)acetyl, N-(4-ethyl-2,3-dioxo-1-piperazinocarbonyl)-D-methionyl, D-2-(4-(2-phenylethyl)-2,3-dioxo-1-piperazinocarboxamido)phenylacetyl, D-2-(4-ethyl-2,3-dioxo-1-piperazinocarboxamido)-2-(4-benzoyloxyphenyl)acetyl, 2,5-bis(4-ethyl-2,3-dioxo-1-piperazinocarboxamido)pentanoyl, 2-(4-ethyl-2,3-dioxo-1-piperazinocarboxamido)-3-(N-methylcarbamoyl)-propionyl, 2,3-bis(4-ethyl-2,3-dioxo-1-piperazinocarboxamido)propionyl, 2(4-ethyl-2,3-dioxo-1-piperazinocarboxamido-3-chloropropionyl, 2-(4-ethyl-2,3-dioxo-1-piperazinocarboxamido)-2-(4-n-octanoylphenyl)acetyl, 2-(4-ethyl-2,3-dioxo-1-piperazinocarboxamido)-3-sulfamoylpropionyl, 2-(4-ethyl-2,3-dioxo-1-piperazinocarboxamido)-3-((1-methyl-1H-tetrazol-5-yl)thio)propionyl, 2-(4-ethyl-2,3-dioxo-1-piperazinocarboxamido)acetyl, D-2-(4-hydroxyethyl)-2,3-dioxo-1-piperazinocarboxamido)-2-phenylacetyl, D-2-(4-(2-chloroethyl)-2,3-dioxo-1-piperazinocarboxamido)-2-phenylacetyl, 2-(4-ethyl-2,3-dioxo-1-piperazinocarboxamido)-3-(ethoxycarbonylmethylcarbamoyl)propionyl, 2-(4-ethyl-2,3-dioxo-1-piperazinocarboxamido)-3-(thienylacetamido)propionyl, 2-(4-ethyl-2,3-dioxo-1-piperazinocarboxamido)-3-(2-(1H-tetrazol-1-yl)acetamido)propionyl, 2-(4-ethyl-2,3-dioxo-1-piperazinocarboxamido)-2-(1H-tetrazol-1-yl)acétyl, 2((2-oxo-3-furfurylideneamidoimidazolidin-1-yl)carboxamido)-2-phenylacetyl, 2-(2-oxo-3-furfurylideneaminoimidazolidin-1-yl)carboxamido-2-(4-hydroxyphenylacetyl, 2-((2-oxo-3-furfurylideneaminoimidazolidin-1-yl)carboxamido)-2-(4-hydroxysulfonyloxyphenyl)acetyl, 2-((2-oxo-3-thiophen-2-aldoimino)imidazolidin-1-yl)carboxamido)-2-phenylacetyl, 2-((2-oxo-3-furfurylideneaminoimidazolidin-1-yl)carboxamido)-2-thienylacetyl, 2-(3-methylsulfonyl-2-oxoimidazolidine-1-carboxamido)-2-phenylacetyl, 2-((2-oxo-3-furfurylideneaminoimidazolidin-1-yl)carboxamido)-2-(2-amino-4-thiazolyl)acetyl, 2-((2-oxo-3-furfurylideneaminoimidazolidin-1-yl)carboxamido-2-(2-chloroacetamido-4-thiazolyl)acetyl, 2-((3-mesyl-2-oxoimidazolidin-1-yl)carboxamido)-2-phenylacetyl, 2-((2-oxo-3-(thiophen-2-aldoimino)imidazolidin-1-yl)carboxamido)-2-thienylacetyl, 2-((3-mesyl-2-oxoimidazlidin-1-yl)carboxamido)-2-thienylacetyl, D-2-((2-oxo-3-furfurylideneaminoimidaazolidin-1-yl)carboxamido)propionyl, 2-(4-hydroxy-6-methylnicotinamido)-2-phenylacetyl, 2-(4-hydroxy-6-methylnicotinamido)-2-(4-hydroxyohenyl)acetyl, 2-(5,8-dihydro-2-(4-formyl-1-piperazinyl)-5-oxopyrido(2,3-d)pyrimidine-6-carboxamido)-2-phenylacetyl, 2-(3,5-dioxo-1,2,4-triazine-6-carboxyamido)-2-(4-hydroxyphenyl)-acetyl, 2-(3-furylideneamino-2-oxoimidazolidine-1-carboxamido)-2- phenylacetyl, 2-(coumarine-3-carboxamido)-2-phenylacetyl, 2-(4-hydroxy-7-methyl-1,8-naphthyridine-3-carboxamido)-2-phenylacetyl, 2-(4-hydroxy-7-trifluoromethyl-quinoline-3-carboxamido)-2-phenylacetyl, N-(2-(2-amino-4-thiazolyl)acetyl)-D-phenylglycyl, 2-(6-bromo-1-ethyl-1,4-dihydro-4-oxo-thieno (2,3-b)pyridine-3-carboxamido)-2-phenylacetyl, 2-(2-(2-amino-4-thiazolyl)acetamido)-2-phenylacetyl, 2-(2-(2-chloroacetamido-4-thiazolyl)acetamido)-2-phenylacetyl, 2-(2,5-dioxo-1,2,4-triazino-6-carboxamido)-2-thienylacetyl, 2-(2,4-dioxopyrimidino-5-carboxamido)-2-thienylacetyl, 2-(6-hydroxy-1,5-naphthyridinylcarboxamido)-2-phenylacetyl, 2-(2-(4-ethyl-2,3-dioxo-1-piperazinocarboxamido)-2-thienylacetamido)-2-phenylacetyl, 2-(2-ureido-2-thienylacetamido)-2-phenylacetyl, 2-(2-ureido-2-thienylacetamido)-2-(4-hydroxysulfonyloxyphenyl)acetyl, 2-(2-ureido-2-thienylacetamido)-2-(4-hydroxyphenyl)acetyl, 2-(N-carbobenzoxyprolylamino)-2-furylacetyl, α-(thienylmethylcarbonyl)alanyl, 2-(4-chlorobenzoylureido)-2-thienylacetyl, 2-(2-thienylacetamido)acetyl, N-benzylcarboxamido-D-alanyl, N-(4-hydroxybenzoyl)-D-alanyl, 2-(4-chlorobenzamido)propionyl, 2-(4-aminobenzamido)-acetyl, N-(4-ethyl-2,3-dioxo-1-piperazinocarbonyl)-methionyl-D-phenylglycyl, D-2-(2-(2,6-dichlorophenylthio)acetamido)-2-phenylacetyl, 2-(carbamoyl)amino-2-thienylacetyl, N-carbamoyl-D-phenylglycyl, 2-(3-methyl-carbamoyl-3-methyl-1-ureido)-2-phenylacetyl, 2-(3-methylcarbamoyl-3-methyl-1-ureido)-2-(4-hydroxy)phenylacetyl, 2-(3-methylcarbamoyl-3-methyl-1-ureido)-2-thienylacetyl, 2-(3-(2-hydroxybenzoyl)-1-ureido)-2-phenylacetyl, 2-(3-(2-benzyloxybenzoyl)-1-ureido)-2-(4-hydroxysulfonyloxyphenyl)acetyl, 2-(3-(2-hydroxybenzoyl)-1-ureido)-2-(4-hydroxyphenyl)acetyl, 2-(3-(2-benzyloxybenzoyl)-1-ureido)-2-phenylacetyl, 2-(3-(2-benzyloxybenzoyl)-1-ureido-2-(4-hydroxyphenyl)acetyl, D-2-(2-(benzyloxycarboxamido)-2-(benzyloxycarbonyl)-ethanesulfonamido)-2-phenylacetyl or N-mesyl-D-phenylglycyl.

Furthermore the acyl group includes, for example, N-(2-amino-4-thiazolyl)-2-methoximinoacetyl)-D-alanyl, N-(2-(2-amino-4-thiazolyl)-2-methoximinoacetyl)-D-phenylglycyl, 2-(2-amino-4-thiazolyl)-2-(2-(2-amino-4-thiazolyl)-2-methoxyiminoacetamido)acetyl, 2-(2-chloroacetamido-4-thiazolyl)-2-(2-(2-chloroacetamido-4-thiazolyl)-2-methoxyiminoacetamido)acetyl, 2-(2-chloroacetamido-4-thiazolyl)-2-methoxyiminoacetyl, 2-(2-amino-4-thiazolyl)-2-methoxyiminoacetyl, 2-(2-amino-4-thiazolyl)-2-oxyiminoacetyl, 2-thienyl-2-methoxyiminoacetyl, 2-furyl-2-methoxyiminoacetyl, 2-(4-hydroxyphenyl)-2-methoxyiminoacetyl, 2-phenyl-2-methoxyiminoacetyl, 2-phenyl-2-oxyiminoacetyl, 2-thienyl-2-oxyiminoacetyl, 2-thienyl-2-dichloroacetyloxyiminoacetyl, 2-(4-(γ-D-glutamyloxy)phenyl)-2-oxyiminoacetyl, 2-(4-(3-amino-3-carboxypropoxy)phenyl)-2-oxyiminoacetyl, 2-thienyl-2-(3-morpholinopropyloxyimino)acetyl, 2-(2-amino-4-thiazolyl)-2-methoxyiminoacetamido)-2-phenylacetyl, 2-(2-(2-chloroacetamido-4-thiazolyl)-2-methoxyiminoacetamido)-2-phenylacetyl or 2-(2-(2-amino-4-thiazolyl)-2-methoxyiminoacetamido)acetyl.

The acyl group of the already mentioned formula

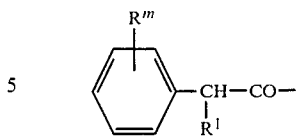

includes, for example, α-sulfophenylacetyl, α-sulfoxyphenylacetyl, α-hydroxyphenylacetyl, α-sulfamoylphenylacetyl, α-phenoxycarbonylphenylacetyl, α-(p-tolyloxycarbonyl)phenylacetyl, α-formyloxyphenylacetyl, α-carboxyphenylacetyl, α-benzyloxycarbonylphenylacetyl or 2-(N,N-dimethylsulfamoyl)-2-phenylacetyl.

The acyl group of the formula $$R^n-R^o-CH_2-CO-$$

already mentioned in section (e) includes, for example, cyanoacetyl, phenylacetyl, phenoxyacetyl, trifluoromethylthioacetyl, cyanomethylthioacetyl, 1H-tetrazolyl-1-acetyl, 2-thienylacetyl, 2-(2-amino-4-thiazolyl)acetyl, 2-(2-chloroacetamido-4-thiazolyl)acetyl, 2-(2-chloroacetamido-4-thiazolyl)acetyl, 4-pyridylthioacetyl, 2-thienylthioacetyl, 3,5-dichloro-1,4-dihydro-4-oxopyridine-1-acetyl, β-carboxyvinylthioacetyl, 2-(2-aminomethylphenyl)acetyl, 2-(2-N-carbobenzoxyaminomethylphenyl)acetyl, 2-(2-ureidomethylphenyl)acetyl, 2-(2-(2-oxoimidazolidine-1-yl)carbonylaminomethylphenyl)acetyl, 2-(2-(2-oxo-3-benzylideneaminoimidazolidine-1-yl)carboxyaminomethylphenyl)acetyl, 2-(5,6-dihydro-1,4-oxathiin-2-yl)acetyl, 2-(2,5-dioxopyrrolidine-3-yl)acetyl, 2-succinimidoacetyl or 2-(1-acetyl-2,4-dioxo-imidazolidine-3-yl)acetyl.

The amino and/or carboxyl group in the acyl group described above may optionally carry a protective group.

Carboxyl protection groups include all groups generally used in organic chemistry for the protection of carboxyl groups, such as ester groups or silyl groups. Examples for such groups are methyl, ethyl, propyl, isopropyl, t-butyl, t-amyl, benzyl, p-nitrobenzyl, p-methoxybenzyl, benzhydryl, phenacyl, phenyl, p-nitrophenyl, methoxymethyl, ethoxymethyl, benzyloxymethyl, acetoxymethyl, pivaloyloxymethyl, β-methylsulfonylethyl, methylthiomethyl, trityl, β,β,β-trichloroethyl, β-iodoethyl, trimethylsilyl, dimethylsilyl, acetylmethyl, p-nitrobenzoylmethyl, p-mesylbenzoylmethyl, phthalimidomethyl, propionyloxymethyl, 1,1-dimethylpropyl, 3-methyl-3-butenyl, succinimidomethyl, 3,5-di-t-butyl-4-hydroxybenzyl, mesylmethyl, benzenesulfonyl-methyl, phenylthiomethyl, dimethylaminomethyl, pyridine-1-oxide-2-methyl, methylsulfinylmethyl, bis(p-methoxyphenyl)methyl, or 2-cyano-1,1-dimethylethyl. Especially preferred carboxyl protection groups are benzyl, β,β,β-trichloroethyl, p-nitrobenzyl, p-methoxybenzyl, trimethylsilyl, dimethyl-t-butylsilyl, phenacetyl or acetonyl.

The amino protecting groups include all known groups which are used in the field of β-lactams or with peptide synthesis. Examples for such amino protective groups are phthaloyl, p-nitrobenzoyl, p-t-butylbenzoyl, p-t-butylbenzenesulfonyl, benzenesulfonyl or toluenesulfonyl, aliphatic acyl groups such as formyl, acetyl, propionyl, monochloroacetyl, dichloroacetyl, trichloroacetyl, methanesulfonyl, ethanesulfonyl, trifluoroacetyl, maloyl or succinyl, esterified carboxyl groups such as methoxycarbonyl, ethoxycarbonyl, t-butoxycarbonyl, isopropoxycarbonyl, 2-cyanoethoxycarbonyl, β,β,β-trichloroethoxycarbonyl, benzyloxycarbonyl, p-nitrobenzyloxycarbonyl, p-methoxybenzyloxycarbonyl, diphenylmethyloxycarbonyl, acetylmethyloxycarbonyl, isobornyloxycarbonyl or phenyloxycarbonyl, methylene groups such as (hexahydro-1H-azepin-1-yl)methylene; sulfonyl groups such as 2-amino-2-carboxyethylsulfonyl, or trityl, 2-nitrophenylthio, benzylidene, 4-nitrobenzylidene, di or trialkylsilyl, benzyl or p-nitrobenzyl. Especially preferred amino protecting groups are monochloroacetyl, benzyloxycarbonyl, p-methoxybenzyloxycabonyl, p-nitrobenzyloxycarbonyl, t-butoxycarbonyl or trityl.

Referring to the aforementioned alkoxy groups, methoxy or ethoxy are preferred.

Thus, the substituents $R^1$ and $R^2$ in the azetidin-2-ones of the general formula I can be generally, as mentioned in claim 1, independently from each other, hydrogen, or an organic radical linked to the ring carbon atom via a carbon, nitrogen or oxygen atom, whereby these radicals can be selected from the general and detailed definitions mentioned hereinbefore. The same thing is true for the substituents $R^1$ and $R^2$ and for the additional substituents $R^3$ of 4-acyloxyazetidin-2-ones used as starting materials in the inventive process and shown in the general formula II.

For the preparation of preferred azetidin-2-ones of the formula I starting materials of formula II are used, wherein $R^1$ and $R^2$ are, independently from each other, hydrogen, alkyl with 1 to 7 carbon atoms or alkoxy with 1 to 7 carbon atoms and wherein $R^3$ is hydrogen or alkyl with 1 to 7 carbon atoms.

Furthermore, also the preparation of azetidin-2-ones of the general formula I is preferred, which can be prepared from 4-acyloxyazetidin-2-ones of the general formula II, wherein $R^1$ is an amino group or a protected amino group, $R^2$ is hydrogen, alkyl with 1 to 7 carbon atoms or alkoxy with 1 to 7 carbon atoms and wherein $R^3$ is hydrogen or alkyl of 1 to 7 carbon atoms.

Within the two aforementioned groups of compounds the use of compounds of formula II is preferred, wherein one of the substituents $R^1$ and $R^2$ is hydrogen.

If $R^1$ is a protected amino group, in the process of the invention preferably compounds of formula II are used, the amino group of which is protected by a hydrocarbonoxycarbonyl group or a hydrocarboncarbonyl group. Specially preferred are protected amino groups $R^1$, the protective groups of which are phenoxyacetyl, benzyloxycarbonyl or t-butoxycarbonyl.

The process of the invention is preferably the last step of a whole process corresponding to variant (B) of the aforementioned reaction scheme.

Within this whole process, starting materials, intermediates and reaction products are preferred, wherein $R^1$ is an amino group substituted by an acyl substituent or a protective group for amino, as already mentioned. Specially preferred substituents $R^1$ are amino groups protected by benzyloxycarbonyl or t-butoxycarbonyl. The substituent $R^2$ is preferably hydrogen or methoxy. As substituents $R^3$ methyl and ethyl is specially preferred. The substituent $R^4$ may be hydrogen or any organic residue. As an organic residue the substituent may be exemplified by any carboxyl protecting group as already defined or also any ester residue which is cleaved at usual reaction conditions. Among these ester residues cleavable at usual reaction conditions there are residues which normally are not useful as protecting groups in organic chemistry. Examples of such residues $R^4$ are methyl, ethyl, propyl, isopropyl, n-butyl, pentyl, decyl, dodecyl, tetradecyl, cyclopentyl, cyclohexyl, alkoxyalkyl, alkanoyloxymethyl or alkenyl. Especially useful residues $R^4$ are methyl and ethyl.

An especially preferred way of performance of process (B) aforementioned in the reaction scheme will now be described.

Starting materials are 6-aminopenicillanic acid ($R^1$=amino, $R^2$=hydrogen), 6-amino-6-methoxyoenicillanic acid ($R^1$=amino, $R^2$=methoxy), the natural penicillin V ($R^1$=PhOCH$_2$CONH—, $R^2$=hydrogen, $R^4$=hydrogen) and the natural penicillin G ($R^1$=PhCH$_2$CONH—, $R^2$=hydrogen, $R^4$=hydrogen) as well as their 6-methoxy derivatives.

The first reaction step, which is not shown in the reaction scheme, involves acylation of the amino group of 6-amino-penicillanic acid or 6-amino-6-methoxypenicillanic acid, wherever these starting materials are used. Such acylations are carried out according to known procedures. For the purposes of invention an acylation using di-t-butyl pyrocarbonate is preferred, leading to compounds with an amino group at the 6-position which is protected by t-butyloxycarbonyl. Such a so-called BOC-ylation is carried out in water or in an organic solvent, for example dioxane, tetrahydrofuran, an amide, such as N,N-dimethylacetamide or N,N-dimethylformamide, an alcohol, such as t-butanol, or a ketone, such as acetone or methylethyl ketone, whereby also mixtures of such solvents or other solvents may be used and which do not interfere with the reaction. The reaction temperature is suitable between about 20° and 40° C. An upper limit is practically only given by the decomposition of di-t-butyl pyrocarbonate used for the acylation.

The acylation reaction is base catalyzed and it is preferably carried out in the presence of basic catalysts. Examples are inorganic or organic bases, such as alkali hydroxides, alkali oxides, earth alkali hydoxides, earth alkali oxides, alkali alcoholates, earth alkali alcoholates, alkali carbonates, earth alkali carbonates, aluminum alkyls, organic amines and tetraalkylammonium salts, such as triethylamine, diisopropylethylamine, triisopropylamine, pyridine, N,N-dimethylaniline, quinoline, N,N-dimethylaminopyridine or 1,8-diazabicylo(4,4,-4)undec-7-ene. The next step of the procedure (A) which is shown in the aforementioned reaction scheme consists of an esterification of the acylated amino compound (VIII) obtained in the above mentioned way. Such an esterification, for example, is carried out using a common diazo compound. The residue $R^4$ is—as already mentioned—not critical—for the proceeding of the reaction, thus, for this esterification any reactive and/or relatively stable compounds may be used, such as diazomethane or diphenyldiazomethane. The esterification is carried out in a solvent which does not interfere with the reaction. Examples of solvents are dioxane or tetrahydrofuran, an alcohol, such as methanol or ethanol, a halogenated hydrocarbon, such as methylene chloride or chloroform, or an ether, such as diethyl ether. Naturally, also mixtures of these solvents can be used. The reaction proceeds at mild conditions, i.e. generally at temperatures of about −30° C. and +50° C.

The esterification can also be carried out by reaction of the acylated amino compound (VIII) with an excess of an inorganic or organic base and a halogenated compound of the general formula RX, wherein X is, for example, Cl, Br, I, CH$_3$SO$_2$O—, C$_6$H$_5$SO$_2$O— or tolyl-SO$_2$O—. Furthermore, esters of sulfuric acid of the general formula R$^4$OSO$_2$OR$^5$ may be used. Examples for the applied bases are those described in the aforementioned acylations. This type of esterification can be carried out with or without solvent. Examples of useful solvents are amides, such as dimethylformamide, dimethylacetamide, nitriles, such as acetonitrile, ketones, such as acetone, or also water. Naturally, also mixtures of solvents may be used again. Again, this esterification is preferably carried out at mild conditions, i.e. at temperatures of about 0° C. to 60° C. The aforementioned reaction sequence consisting of initial acylation and subsequent esterification may be reversed also, naturally.

After the acylation and esterification the obtained compound of the formula VII is then sulfoxidized, furnishing a compound of the formula VI. The oxidation agents for this sulfoxidation include all reagents capable of converting sulfide groups into sulfoxide groups, for example, hydrogen peroxide, organoperacids, especially percarboxylic acids, such as peracetic acid, perbenzoic acid, chloroperbenzoic acid or monoperphthalic acid, oxidating inorganic acids or their salts, such as nitric acid, chromic acid, or potassium permanganate, or alkali metal hypochlorites, such as sodium hypochlorite. The desired sulfoxidation can be also carried out by an anodic oxidation. The sulfoxidation is carried out preferably in an inert solvent, for example in a halogenated hydrocarbon, such as methylene chloride, chloroform or carbon tetrachloride, an alcohol, such as methanol or ethanol, a ketone, such as acetone, an ether, such as diethyl ether, dioxane or tetrahydrofuran, an amide, such as dimethylformamide, a sulfone, such as dimethyl sulfone, a liquid organic carboxylic acid, such as acetic acid, or also water. Naturally, again mixtures of solvents can be used, whereby aqueous mixtures are preferred, for example aqueous acetic acid. It is convenient to use temperatures of about −20° C. to +50° C. in such a sulfoxidation. Temperatures of from about 0° C. to room temperature are preferred.

The compound of the formula (VI) obtained by the above mentioned sulfoxidation is then subjected to a ring opening and after this stage the two variants (A) and (B) proceed separately as shown by the reaction scheme. Process (A) is mentioned here only to illustrate the state of technique. Thus, the ring opening of the process (B) will now be described.

In order to achieve such a ring opening, a compound of the formula (VI) is reacted in the presence of a carboxylic acid of the general formula R$^3$—COOH and in presence of an organic phosphite, such as trialkyl phosphite or triarylphosphite, at elevated temperature. It has been found, that the oxazoline side products which are generally formed within these processes in larger amounts and which interfere considerably, can be entirely avoided, when instead of of the acetylamino compounds (VI) (R$^1$=acetylamino) used so far, protected acylamino compounds are used, namely and preferably carbamates having an amino group R$^1$ which, for example, is protected by t-butoxycarbonyl, benzyloxycarbonyl, or p-nitrobenzyloxycarbonyl. Especially the use of a benzyloxycarbonyl or a p-nitrobenzyloxycarbonyl protective group bears the advantage that such protecting groups can be removed at the final stage of the reaction sequence by mild hydrogenolysis. Especially the above mentioned type of procedure of the ring opening provides a special advantage in such a multistep procedure, namely that of a nonformation of the mentioned undesired side products. Consequently, extensive purification methods can be avoided. The use of the above mentioned and selected amino-protecting groups represents therefore a substantial improvement of the ring opening reaction and also revalorizes such a multistep procedure substantially.

Examples of trialkylphosphites used in the above mentioned ring opening reaction are trimethyl phosphite or triethyl phosphite, whereas the triaryl phosphites are preferably exemplified by triphenyl phosphite. Other phosphites also may be used. Examples are dimethylphenyl phosphite or dimethylbutyl phosphite.

The ring opening reaction may be carried out with or without solvent. If a solvent is used, examples are dioxane, amides, such as N,N-dimethylacetamide or N,N-dimethylformamide, aliphatic hydrocarbons, such as benzene or toluene, alcohols, such as t-butanol, or ketones, such as isopropyl methyl ketone. Naturally, mixtures of solvents may also be used.

The reaction temperature is not especially critical. Conveniently temperatures of about 70° C. to 150° C. are used.

Compound (V) obtained in the above mentioned ring opening reaction is then isomerized according to process (B).

Such an isomerisation is normally carried out in organic solvents, for example in amides, such as N,N-dimethylacetamide or N,N-dimethylformamide, alcohols, such as t-butanol, ketones, such as acetone, aromatic hydrocarbons, such as toluene, or chlorinated aliphatic hydrocarbons, such as methylene chloride, chloroform or carbon tetrachloride. Naturally, again solvent mixtures may be used.

The reaction temperature is conveniently between about −20° C. and +50° C.

The isomerisation is also base catalyzed. Useful catalysts include inorganic as well as organic bases, as they were mentioned at the acylation step. The bases are used commonly only in relatively small amounts, whereby often 0.01 to 0.2 molar equivalents, relatively to compound of the formula (V), are sufficient.

Optionally, the isomerisation can also be carried out together with the ring opening process, by carrying out such a ring opening reaction in the presence of a base as catalyst. In this way from compound of the formula (VI) a compound of formula (IV) is obtained directly.

Compound (IV) obtained by the above mentioned way is then ozonolyzed or oxidized to afford a compound of formula (III).

Preferred oxidation agents are for example ozone, alkali permanganates, such as potassium permanganate or sodium permanganate, earth alkali permanganates, such as barium permanganate, osmium tetroxide or lead tetraacetate.

Normally, this oxidation reaction is carried out in presence of a solvent. Examples of solvents are dioxane, tetrahydofuran, amides, such as N,N-dimethylformamide or N,N-dimethylacetamide, aromatic hydrocarbons, such as benzene or toluene, ketones, such as acetone, amines, such as pyridine, alcohols, such as methanol, ethanol, propanol, isopropanol or butanol, chlorinated hydocarbons, such as methylene chloride, chloroform or carbon tetrachloride, or also water. Naturally, mixtures of solvents can also be used. Preferred are mixtures with water.

The oxidizing agent is generally used in amounts of 1 to 4 molar equivalents, preferably of 1 to 1,2 molar equivalents, relatively to the relevant compound of the formula (IV). Ozone generally is used in excess, naturally.

The reaction temperature is not specially critical. Usually the reaction is carried out with ice cooling or at room temperature. When permanganate is used as an oxidizing agent, it is convenient to carry out the reaction in a buffered solution at an approximately neutral pH value in order to avoid the decomposition of product. If ozone is used as an oxidizing agent, normally, the solvent is chloroform, methylene chloride or carbon tetrachloride. An excess of ozone is thereby used. It is then, for example, decomposed with dimethyl sulfide.

The next step in the above mentioned reaction sequence is a solvolysis of the relevant compound of formula (III) affording the corresponding compound of the formula (II).

Such a solvolysis is usually carried out in a suitable solvent and it can be accelerated by the presence of acidic or basic catalysts. Examples thereof are inorganic bases, such as alkali hydroxides, alkali carbonates, earth alkali hydroxides, earth alkali carbonates, for examples the hydroxides or carbonates of lithium, sodium, potassium, calcium or magnesium, organic bases or quaternary ammonium salts or also basic ion exchange resins. Examples for acids suitable as catalysts are inorganic acids and their salts, such as hydrochloric acid, sulfuric acid, phosphoric acid, zinc chloride, zinc sulfate, iron (III) chloride or iron (III)-sulfate, organic acids, such as acetic acid, toluenesulfonic acid or trifluoroacetic acid, silica gel or ion exchange resins. Suitable solvents are, for example, water, alcohols, such as methanol, ethanol, propanol, tetrahydrofuran or dioxane, or also esters, such as ethyl acetate. Naturally, again solvent mixtures may be used. The reaction normally proceeds at mild conditions, i.e., for example with ice cooling or at room temperature up to slightly elevated temperature.

The aforementioned solvolysis may also be accomplished without isolating the oxidation product of the formula (III) obtained in the preceeding oxidation reaction. In this case the relevant compound of formula (IV) is subjected to a simultaneous oxidation and solvolysis by carrying out the process in a solvolysing solvent, for example in methanol or in a mixture of methanol and water. This joint proceeding is preferably carried out over an extended period.

Furthermore, the solvolysis step can also be carried out simultaneously with the process of the invention by using, at the same time, a complex metal hydride, comprising reactive hydride ions, as it is defined for this process. In such a case, naturally, the solvolysis product is not isolated, but directly converted by the process of the invention to the relevant azetidin-2-one of the mentioned general formula I.

The invention is described by examples, as follows.

Examples for illustration of the process of the invention

EXAMPLE 1

Preparation of azetidin-2-one

Into a solution of 25.8 g (0.2 mol) 4-acetoxy-azetidin-2-one in 200 ml of water, at −20° C. with stirring and within 1 hour 11.4 g (0.3 mol) sodium borohydride is added in small portions, in order to maintain the reaction temperature between −10° C. and 0° C. Then, the mixture is stirred for 90 minutes with ice cooling, whereby the gas evolution comes to an end. The reaction mixture is filtered through a glass filter and the cooled filtrate saturated with 70 g of sodium chloride. The cool aqueous solution is then extracted with methylene chloride in a liquid-liquid Keberle extractor for 15 hours. The extraction residue weighing 10.4 g is crystallized from 350 ml of ether after addition of a little pentane. The yield is 8.7 g (61%). The melting point is 68° to 73° C. A destillation in high vacuo furnishes material of melting point 73° to 74° C. and a boiling point of about 80° C. at 4 mbar. IR spectrum in $CH_2Cl_2$: 3420, 2980, 2920, 1765 and 1185 $cm^{-1}$.

EXAMPLE 2

Preparation of azetidin-2-one

To a solution of 5 g (39 mmol) 4-acetoxyazetidin-2-one in 95 ml of dry tetrahydrofuran, at room temperature and with stirring within 15 minutes a 0.16 molar solution of zinc borohydride in dry ethyl ether is added dropwise. The reaction mixture is refluxed for 2 hrs, carefully saturated sodium chloride solution is added and then extracted with 70 ml of diethyl ether. For a complete extraction the aqueous layer is extracted in a liquid-liquid Keberle extractor for 4 hours using methylene chloride. The combined extracts are dried over sodium sulfate and at ambient pressure the solvent removed through a destillation column. The crystalline residue of 1.72 g (63%) is obtained after short drying in vacuo at 17 mbar. It is consistent with the product of example 1 and has the same physical constants as well as the same IR spectrum.

EXAMPLE 3

Preparation of azetidin-2-one

To a solution containing 650 mg (5 mmol) of 4-acetoxyazetidin-2-one in 30 ml of methylene chloride at room temperature and dropwise a solution of 1.45 g tetraethylammonium borohydride in 60 ml of methylene chloride is added. The reaction mixture is stirred for 60 minutes at room temperature, until the reaction comes to an end. Then, the mixture is stirred with 100 ml of saturated sodium chloride solution until the gas evolution ceases. The organic layer is separated and the aqueous layer extracted five times with portions of 100 ml of methylene chloride. The combined methylene chloride extracts are dried over sodium sulfate, evaporated at 30° C. in a vacuum rotary evaporator and finally dried in vacuo at 17 mbar. The residue weighing 300 mg (84%) is consistent with the product of example 1 and shows the same physical constants as well as the same IR spectrum.

EXAMPLE 4

Preparation of azetidin-2-one

To a solution of 650 mg (5 mmole) 4-acetoxyazetidin-2-one in 30 ml of water in small portions with stirring 500 mg (10 mmol) potassium borohydride is added at room temperature. After a reaction time of 30 minutes at room temperature the reaction solution is quenched with saturated sodium chloride solution and stirring is continued until gas evolution comes to an end. The formed precipitate is removed by filtration. The aqueous layer is extracted five times with portions of 100 ml of methylene chloride. The combined extracts are dried over sodium sulfate and evaporated in a vacuum rotary evaporator at 30° C. The crystalline residue of 247 mg (69%) shows the physical constants mentioned in example 1, including the same IR spectrum.

EXAMPLE 5

Preparation of 3-methylazetidin-2-one

A solution of 716 mg (5 mmol) 4-acetoxy-3-methylazetidin-2-one in 15 ml of dry tetrahydrofuran is reacted with 30 ml of a 0.16 molar solution of zinc boroydride in dry diethyl ether and the reaction mixture kept under reflux for two hours. The reaction mixture is worked up as mentioned in example 2, whereby 340 mg (80%) of a noncrystalline oil is obtained. IR spectrum in methylene chloride: 3420, 2980, 1750, 1380 and 1180 cm$^{-1}$.

EXAMPLE 6

3-Ethylazetidin-2-one

To a solution of 785 mg (5 mmol) 4-acetoxy-3-ethylazetidin-2-one in 15 ml of absolute tetrahydrofuran at room temperature 30 ml of a 0.16 molar solution of zinc borohydride in diethyl ether is dropwise added. The mixture is then refluxed for two hours. After work up according to example 2, followed by a "Kugelrohr" destillation at 130° C. and 16 mbar, 293 mg (59%) of title compound is obtained as a non-crystalline oil. IR spectrum in methylene chloride: 3420, 2980, 1760, 1460, 1370 and 1190 cm$^{-1}$.

EXAMPLE 7

3,3-Dimethylazetidin-2-one

To a solution of 785 mg (5 mmol) 4-acetoxy-3,3-dimethylazetidin-2-one in 30 ml of water at room temperature and with stirring 540 mg (10 mmol) potassium borohydide is added in small portions. After 30 minutes to the reaction mixture saturated sodium chloride solution is added and stirring continued until gas evolution comes to a complete end. By work up of the reaction mixture as mentioned in example 4 752 mg (76%) of title compound as a crystalline solid of a melting point of about 30° C. is obtained. IR spectrum in methylene chloride: 3400, 2960, 2920, 1760, 1380, 1360, and 1180 cm$^{-1}$.

EXAMPLE 8

3,3-Dimethylazetidin-2-one

To a solution of 5 g (32 mmol) 4-acetoxy-3,3-dimethylazetidin-2-one in 96 ml of dry tetrahydrofuran at room temperature 200 ml of a 0.16 molar solution of zinc borohydride in dry diethyl ether is dropwise added. The reaction mixture is refluxed for 2 hours and then worked up as described in example 2. After a "Kugelrohr" destillation at 120° C. and 16 mbar 2.47 g (78%) of a crystalline solid of a melting point of about 30° C. is obtained. The IR spectrum is identical with the IR spectrum of example 7.

EXAMPLE 9

3,3-Dimethylazetidin-2-one

To a solution of 785 mg (5 mmol) 4-acetoxy-3,3-dimethylazetidin-2-one in 10 ml of methylene chloride at room temperature and dropwise with stirring a solution of 1.45 g of tetraethylammonium borohydride in 60 ml of methylene chloride is added. The reaction mixture is stirred for 60 minutes at room temperature. After work up of the reaction mixture as mentioned in example 3, 473 mg (96%) of title compound is obtained. The IR spectrum is identical to the IR spectrum of example 7.

EXAMPLE 10

3,3-Dimethylazetidin-2-one

To a solution of 157 mg (1 mmol) 4-acetoxy-3,3-dimethylazetidin-2-one in 5 ml tetrahydrofurane (freshly distilled over lithium aluminum hydride) with stirring at 0° C., within 5 minutes 19 mg (0.5 mmol) lithium aluminum hydride is added in small portions. Then the reaction mixture is stirred for 15 minutes at 0° C. The reaction mixture is diluted with 0.5 ml of ethyl acetate, 30 ml of methylene and 20 ml of saturated aqueous sodium chloride solution and the pH adjusted to a value of 2. The organic layer is separated and extracted twice with portions of 20 ml of methylene chloride. The combined organic extracts are evaporated and thus, 92 mg of crude product as a noncrystalline residue is obtained. The residue is then chromatographed on 3 g of silica gel with toluene-ethyl acetate (1:1) (20 fractions, 3 ml each), whereby 30 mg (30%) of pure title compound with IR and NMR spectra identical to those of example 7 are obtained.

EXAMPLE 11

Preparation of 3,3-dimethylazetidin-2-one

To a solution of 157 mg (1 mmol) 4-acetoxy-3,3-dimethylazetidin-2-one in 5 ml of water, with stirring at room-temperature 186 mg (3 mmol) sodium cyanoborohydride is added. Then within 5 hours a 1N solution of hydrogen chloride in water is dropwise added, in order to maintain the pH value between 2 and 4. To the mixture 1.0 g of sodium chloride is added and then it is extracted three times with portions of 30 ml of methylene chloride. The combined organic extracts are dried over magnesium sulfate, filtered and evaporated in vacuo. The noncrystalline residue of 105 mg is purified as mentioned in example 8, whereby 56 mg (56%) of pure title compound with IR and NMR spectra identical to those of example 7 are obtained.

EXAMPLE 12

(S)-3-Phenoxyacetamidoazetidin-2-one

A solution of 278 mg (1 mmol) (3S,4S)-4-acetoxy-3-phenoxyacetamido-azetidin-2-one (prepared according to Tetrahedron Letters 1978, 4059) in 5 ml of isopropanol is diluted with 10 ml of water, 76 mg sodium borohydride added in small portions and then stirred at 0° C. for 30 minutes. The mixture is then diluted with 15 ml of saturated sodium chloride solution and then extracted three times with 30 ml portions of methylene chloride. The methylene chloride extracts are combined, dried over sodium sulfate and evaporated in vacuo, leaving 198 mg of residue. Chromatography on 5 g of silica gel using toluene-ethyl acetate (1:2) affords 154 mg (70%) of title compound of melting point 152° to 153° C. and a $\alpha_{20}{}^D$-value of $-19°$ (methanol, c=1). IR spectrum in methylene chloride: 3420, 3000, 1780, 1700, and 1610 cm$^{-1}$.

EXAMPLE 13

(S)-3-Benzyloxycarbonylamino-azetidin-2-one

A solution containing 278 mg (1 mmol) (3S,3R)-4-acetoxy-3-benzyloxycarbonylaminoazetidin-2-one in 5 ml of isopropanol is diluted with 10 ml of water at 0° C. and to this solution 78 mg (2 mmol) sodium borohydride added in small portions. After stirring of the mixture for 30 minutes at 0° C. 15 ml of a saturated sodium chloride solution is added and the mixture extracted three times with portions of 30 ml of methylene chloride. The methylene chloride extracts are combined, dried over sodium sulfate, affording 201 mg of residue. This residue is chromatographed on 5 g of silica gel using toluene-ethyl acetate (1:2). Thus, 150 mg (68%) of title compound is obtained as a crystalline product of a melting point of 164° C. to 165° C. and a $\alpha_D^{20}$-value of $-18°$ (methanol, c=1). IR spectrum in methylene chloride: 3420, 1775, 1725, 1510 and 1220 cm$^{-1}$.

EXAMPLE 14

(S)-3-t-Butoxycarbonylaminoazetidin-2-one

A solution containing 366 mg (1.5 mmol) (3S,4S)-4-acetoxy-3-t-butyloxycarbonylaminoazetidin-2-one in 7.5 ml of isopropanol is diluted with 15 ml of water. The solution is cooled to 0° C., with stirring in small portions 114 mg (3 mmol) sodium borohydride is added and the reaction mixture stirred for additional 30 minutes at 0° C. The mixture is quenched with 15 ml of saturated aqueous sodium chloride solution and then extracted with portions of 50 ml of methylene chloride. The combined methylene chloride extracts are dried over sodium sulfate and evaporated in vacuo affording 225 mg of a crystalline residue. Recrystallisation of this residue from ethyl acetate and n-hexane furnishes 180 mg (65%) of title compound of melting point of 173° to 175° C. and a $\alpha_D^{20}$-value of $-19°$ (methanol, c=1). IR spectrum in methylene chloride: 3420, 1775, 1720, 1500, 1360, 1230 and 1150 cm$^{-1}$.

EXAMPLE 15

Preparation of (S)-3-t-butyloxycarbonylaminoazetidin-2-one

This example shows a so called one pot process of the invention, wherein besides the cleavage of a 4-acetoxy substituent using a complex metal hydride, also and simultaneously a methyl 2-oxoacetate substituent at the 1-position of the azetidinone nucleus is cleaved by solvolysis.

A solution of 330 mg (1 mmol) of (3S,3R)methyl(4-acetoxy-3-t-butyloxycarbonylaminoazetitin-2-on-lyl)-2-oxoacetate in 5 ml of isopropanol is warmed to 50° C. and diluted with 10 ml of water. To the obtained suspension within 5 minutes at 0° C., with stirring, 100 mg (2.5 mmol) sodium borohydride is added in small portions and then the clear solution stirred at 0° C. for additional 45 minutes. The mixture is diluted with 50 ml of methylene chloride and washed with 10 ml of saturated sodium chloride solution. The aqueous layer is extracted three times with portions of 100 ml of methylene chloride and the combined methylene chloride extracts dried over sodium sulfate. Subsequent evaporation of the solvent in vacuo furnishes 176 mg (95%) of a crystalline crude product. Recrystallisation of this crude product from ethyl acetate and n-hexane affords 105 mg (56%) of title compound of a melting point of 173° to 175° C. and a $\alpha_D^{20}$-value of $-18°$ (methanol, c=1). The IR spectrum of the compound is identical to that of example 14.

EXAMPLE 16

Preparation of (S)-3-benzyloxycarbonylaminoazetidin-2-one

This example again shows a so called one pot process of the invention, wherein besides the cleavage of a 4-acetoxy substituent using a complex metal hydride, also and simultaneously a methyl 2-oxoacetate substituent at the 1-position of the atetidinone nucleus is cleaved by solvolysis. A solution of 780 mg (2.14 mmol) of (3S,3R)methyl(4-acetoxy-3-benzyloxycarbonylaminoazetidin-2-on-1-yl)-2-oxoacetate in 20 ml of hot isopropanol is diluted with 40 ml of water. To the obtained suspension within 5 minutes at 0° C., with stirring, 237 mg (6.25 mmol) sodium borohydride is added in small portions and then the clear solution stirred at 0° C. for additional 30 minutes. The mixture is diluted with 150 ml of methylene chloride and washed with 50 ml of saturated sodium chloride solution. The aqueous layer is extracted three times with portions of 50 ml of methylene chloride and the combined methylene chloride extracts dried over sodium sulfate. Subsequent filtration and evaporation of the solvent in vacuo affords 577 mg of a crystalline residue. This residue is recrystallized from 3 ml of hot isopropanol, furnishing 300 mg (64%) of title compound with a melting point of 164° to 165° C. Chromatography of the mother liquors on 15 g silica gel using toluene-ethyl acetate (1:1) affords 70 mg (15%) of crstalline product, additionally, having a $\alpha_D^{20}$-value of $-18°$ (methanol, c=1). The IR spectrum is identical to that of example 13.

EXAMPLE 17

Multi-step preparation of (S)-3-t-butoxycarbonylaminoazetidin-2-one (a) Preparation of (2R)methyl 2-((3S,4S)-4-acetoxy-3-t-butyloxycarbonylaminoazetidin-2-on-1-yl)-3-methyl-but-3-enoate A mixture containing 3.46 g (10 mmol) (6R)methyl 6-t-butyloxycarbonylaminopenicillanate-β-sulfoxide, 5 ml of trimethyl phosphite and 1.7 ml (30 mmol) acetic acid in 200 ml of pure benzene is refluxed for 40 hours in a nitrogen atmosphere. The mixture is diluted with 50 ml of ethyl acetate and washed with 100 ml of saturated sodium bicarbonate solution. The organic layer is dried over magnesium sulfate, filtered and the solvent removed by evaporation in a rotary evaporator, affording, after drying at 0.025 mbar and 50° C., 4.0 g of a noncrystalline residue. The NMR spectrum of this residue shows (2R)methyl 2-((3S,4S)-4-acetoxy-3-t-butyloxycarbonylaminoazetidin-2-on-1-yl)-(3-methyl-but-3-enoate), contaminated by only a little trimethylthiophosphate.

(b) Preparation of methyl 2-((3S,4S)-4-acetoxy-3-t-butyloxycarbonylaminoazetidin-2-on-1-yl)-3-methyl-but-3-enoate The above mentioned residue is dissolved in 100 ml pure methylene chloride, to the solution 1 ml of triethylamine added and the mixture left at room temperature for 6 hours. The mixture is washed with 50 ml of 2N aqueous hydrogen chloride solution and then rewashed with 50 ml of saturated sodium chloride solution. The organic layer is separated, dried over magnesium sulfate, filtered and the solvent removed by evaporation in a vacuum rotary evaporator, affording 3.7 g of a non-crystalline residue. The NMR spectrum indicates slightly impure (δ=3.6, 3.8 ppm) methyl 2-((3S,4S)-4-acetoxy-3-t-butyloxycarbonylaminoazetidin-2-on-1-yl)-3-methyl-but-3-enoate.

(c) Preparation of methyl((3S,4S)-4-acetoxy-3-t-butyloxycarbonylaminoazetidin-2-on-1-yl)-2-oxoacetate Into a solution of the above mentioned residue in 100 ml of methanol, at $-20°$ C. a mixture of ozone and oxygen was introduced through a tube of 6 mm and with a rate of 0.2 mmol ozone per minute. After a priod of three hours thin layer chromatography indicates a complete reaction. The thus formed crystalline precipitate is collected in a cooled glass filter, whereby complete drying of the collected material is avoided, since the solution contains peroxides. The collected material which is still humid is washed with 20 ml of precooled (−35° C.) methanol and then dried in high vacuo, affording 1.65 g pure crystalline methyl((3S,4S)-4-acetoxy-3-t-butyloxycarbonylaminoazetidin-2-on-1-yl)-2-oxoacetate, having a melting point of 144° to 146° C.

(d) Preparation of (3S)-t-butyloxycarbonylaminoazetidin-2-one

The above mentioned crystalline material is treated as described in example 15, affording 0.61 g of pure (3S)3-t-butyloxycarbonylaminoazetidin-2-one. After crystallisation from ethyl acetate and n-hexane the melting point is 173° to 175° C.

The methanolic peroxide containing mother liquor from the aforementioned reaction step (c) of the ozonolysis, is partly evaporated in a vacuum rotary evaporator to a volume of 25 ml, avoiding stictly a complete evaporation because of the present peroxides. The solution is cooled to 0° C., diluted with 50 ml of water and during 10 minutes 600 mg sodium borohydride added in small portions with stirring at 0° C. Stirring at 0° C. is continued for 50 minutes and then the mixture is quenched with 50 ml of saturated sodium chloride solution and extracted three times with portions of 30 ml of methylene chloride. The combined extracts are dried over magnesium sulfate, filtered and the solvent removed in a vacuum rotary evaporator, affording 0.70 g of a noncrystalline residue. This residue is combined with the non-volatile portion of the mother liquor (0.27 g) obtained according to example 15 and chromatographed on 15 g of silica gel using 10 fractions of ethyl acetate, 5 ml each, followed by 5 fractions of ethyl acetate, 15 ml each, furnishing 0.29 g (3S)-3-butyloxycarbonylaminoazetidin-2-one, additionally. The IR spectrum of the crystalline compound is identical to that of the recrystallized material. The optical roration $\alpha_D^{20}$ (c=1, methanol) is −19° C.

The overall yield of all reaction steps described above, is 0.9 g (48%).

Examples to illustrate the preparation of starting materials

EXAMPLE 18

Preparation of methyl ((3S,4S)-t-butyloxycarbonylaminoazetidine-2-on-1-yl)-2-oxoacetate (starting material of Example 15) and of (3S,4S)-acetoxy-3-t-butyloxycarbonylaminoazetidin-2-one (starting material of Example 14)

(a) Preparation of (R) methyl 6-t-butyloxycarbonylaminopenicillanate-β-oxide (a1) Preparation of (R)-6-t-butyloxycarbonylaminopencillanic acid A suspension containing 1.08 g (5 mmol) 6-aminopenicillanic acid, 1.13 g (5.2 mmol) di-t-butyl pyrocarbonate and 0.7 ml of triethylamine in 10 ml of tetrahydrofuran is quenched with 10 ml of water, whereupon a clear solution is formed. The reaction mixture is stirred for 24 hours at room temperature. The evolution of carbon dioxide ceases after approximately 6 hours. The mixture is diluted with 100 ml of methylene chloride, washed with 30 ml of a 0.2N solution of hydrogen chloride in water. The organic layer is separated and the aqueous layer extracted with 550 ml of methylene chloride. The methylene chloride extracts are combined and dried over sodium sulfate and the solvent removed in vaccum affording 1.6 g (100%) of a noncrystalline solid. IR spectrum in methylene chloride: 3420, 2950, 1800, 1725, 1500 and 1160 cm$^{-1}$.

(a2) Preparation of (R) methyl 6-t-butyloxycarbonylaminopenicillanate

To a solution containing 3.16 g (R)-t-butyloxycarbonylaminopenicillanic acid in 25 ml dry tetrahydrofuran, at 0° C. with stirring, a cooled (0° C.) solution of diazomethane (0.75 molar) in diethyl ether is added until the yellow colour remains and the gas evolution ceases. The crstalline reaction mixture is left at 0° C., the crystals filtered off and dried in vacuo. The mother liquor is crystallized by addition of n-pentane. In this way totally 2.97 g (90%) of title compound of a melting point of 143° to 144° C. is obtained. IR spectrum in methylene chloride; 3420, 2980, 1790, 1750, 1720, 1500 and 1150 cm$^{-1}$.

To a solution of 6.6 g (20 mmol) of the aforementioned (R) methyl 6-t-butyloxycarbonylaminopenicillanate in 200 ml of methylene chloride, with stirring at −10° C., in small portions and within 30 minutes 3.88 g (20 mmol) of solid m-chloroperbenzoic acid is added. The reaction mixture is stirred for additional 30 minutes at 0° C. and then washed subsequently with 150 ml of saturated sodium bicarbonate solution, 100 ml of 10% sodium bisulfite solution and again with 100 ml of saturated sodium bicarbonate solution. Then, the solution is dried over sodium sulfate and then the solvent removed in vacuo, leaving 6.7 g of a crystalline residue. The residue is recystallized from 100 ml of hot isopropanol, affording 6.3 g of title compound. After drying in high vacuo at 50° C. the melting point is 167° to 169° C. IR spectrum in methylene chloride: 3420, 2980, 1800, 1755, 1720, 1500, 1150 and 1040 cm$^{-1}$.

(b) Preparation of (2R) methyl 2-((3S,4S)-4-acetoxy-3-t-butyloxycarbonylaminoazetidin-2-on-1-yl)-3-methylbut-3-enoate A mixture containing 346 mg (1 mmol) (R) methyl 6-t-butyloxycarbonylaminopenicillanate-β-sulfoxide, 0.5 of trimethyl phosphite and 0.17 ml of acetic acid in 20 ml of benzene is refluxed for 30 hours. The mixture is diluted with 10 ml of ethyl acetate and washed with 20 ml of saturated aqueous sodium bicarbonate solution. The organic layer is dried and the solvent removed in vacuo, affording 480 mg of a noncrystalline residue. Chromatography of this residue on 15 g of silica gel using a 7:1 mixture of toluene and ethyl acetate affords 253 mg (72%) of a noncrystalline solid (title compound). IR spectrum in methylene chloride: 3420, 3000, 1790, 1750, 1725, 1500, 1220 and 1155 cm$^{-1}$.

(c) Preparation of methyl 2-((3S,4S)-4-acetoxy-3-t-butyloxycarbonylaminoazetidin-2-on-1-yl)-3-methylbut-2-enoate To a solution of 1.07 g (3 mmol) (2R) methyl 2-((3S,4S)-4-acetoxy-3-t-butyloxycarbonylaminoazetidine-2-on-1-yl)-3-methylbut-3-enoate in 30 ml of methylene chloride, at room temperature 0.3 ml of triethylamine is added and the reaction mixture stirred for 6 hours at room temperature. The reaction mixture is first washed with 15 ml of 1N hydrogen chloride in water and then with 15 ml of saturated sodium chloride solution. The organic layer is dried over sodium sulfate and the solvent removed in vacuo, leaving 1.07 g (100%) of a noncrystalline solid (title compound). IR spectrum in methylene chloride: 3420, 3000, 1790, 1760, 1725, 1505, 1385, 1365, 1215 and 1150 cm$^{-1}$.

(d) Preparation of methyl ((3S,4S)-4-acetoxy-3-t-butyloxycarbonylaminoazetidin-2-on-1-yl)-2-oxoacetate Into a solution of 910 mg (2.5 mmol) of methyl 2-((3S,4S)-4-acetoxy-3-t-butyloxycarbonylaminoazetidin-2-on-1-yl)-3-methylbut-2-enoate in 40 ml of methanol, for 120 minutes at −10° C. in a mixture of ozone and oxygen is introduced at a rate of 0.1 mmol of ozone per minute. The obtained crystalline residue is dissolved by addition of 160 ml of methylene chloride and the solution is washed subsequently with 60 ml of a 10% aqueous sodium bisulfite solution and 60 ml of saturated sodium chloride solution. The organic layer is dried over sodium sulfate and dried in vacuo, affording 640 mg of a noncrystalline solid. Recrystallisation from cold methanol furnishes 613 mg (74%) of pure title compound of a melting point of 144° to 146° C. IR spectrum in methylene chloride: 3400, 3000, 1840, 1765, 1720, 1500, 1360, 1220, 1160 and 1040 cm$^{-1}$.

The aforementioned compound is the starting material of example 15.

(e) Preparation of (3S,4S)-4-acetoxy-3-t-butyloxycarbonylaminoazetidin-2-one

A mixture containing 330 mg (1 mmol, crude material) of methyl ((3S,4S)-4-acetoxy-3-t-butyloxycarbonylaminoazetidin-2-on-1-yl)-2-oxoacetate and 1 ml of water in 50 ml of methanol is left at room temperature for 2 days. Then, the solvent is removed in vacuo, leaving 277 mg of a noncrystalline solid. Chromatography of this residue on 10 g of silica gel using a 3:1 mixture of toluene-ethyl acetate furnished 190 mg (78%) of the colourless title compound as a crystalline solid of a melting point of 113° to 115° C. IR spectrum in methylene chloride: 3400, 3000, 1800, 1750, 1720, 1500, 1220, 1150 and 1030 cm$^{-1}$.

The aforementioned compound is the starting material of example 14.

EXAMPLE 19

Preparation of methyl ((3S,4S)-4-acetoxy-3-benzyloxycarbonylaminoazetidin-2-on-1-yl)-2-oxoacetate (starting material of example 16) and of (3S,4S)-4-acetoxy-3-benzyloxycarbonylaminoazetidin-2-one (starting material of example 13)

(a) Preparation of (R) methyl 6-benzyloxycarbonylaminopenicillanate

To a suspension of 10.8 g (50 mmol) 6-aminopenicillanic acid in 3 ml of water and 27 ml of acetone, subsequently at 0° C. with stirring, 7.5 ml (54 mmol) triethylamine and dropwise 8.0 ml (56 mmol) benzyloxycarbonyl chloride is added. Immediately, a white precipitate is formed. The crystal suspension is stirred at room temperature and is then quenched with 200 ml of methylene chloride. The solution is washed with 100 ml 0.1N hydrogen chloride in water, followed by 100 ml saturated sodium chloride solution. The organic layer is dried over sodium sulfate and filtered and the filtrate evaporated in vacuo to a volume of 150 ml. To the solution obtained in this way containing the crude (R)-6-benzyloxycarbonylaminopenicillanic acid in methylene chloride, at 0° C., a solution of diazomethane in diethyl ether is dropwise added, until the yellow colour remains. Approximately 130 ml of the diazomethane solution is required. Evaporation of the solvent in vacuo furnishes (R) methyl 6-benzyloxycarbonylaminopenicillanate as a solid. The yield is 19.0 g (105%). IR spectrum in methylene chloride: 3500, 3000, 1795, 1755, 1720 and 1500 cm$^{-1}$.

(b) Preparation of (R) methyl 6-benzyloxycarbonylaminopenicillanate β-sulfoxide

To a stirred solution of 18.0 g (50 mmol) crude (R) methyl 6-benzyloxycarbonylaminopenicillanate in 500 ml of methylene chloride, at 0° C., within 15 minutes, 9.7 g (50 mmole) m-chloroperbenzoic acid is added is small portions and the obtained reaction mixture stirred for additional 15 minutes at −10° C. The reaction mixture is subsequently washed with 300 ml of saturated sodium bicarbonate solution, 200 ml of 10% sodium bisulfite solution and again with 150 ml of sodium bicarbonate solution. The organic layer is dried over sodium sulfate, filtered and the solvent removed in vacuo. The residue weighing 18.4 g is chromatographed on 600 g silica gel using a 3:1 mixture of toluene and ethyl acetate, whereby 10 fractions, 600 ml each are used. In this way, 12.25 g (65%, based on 6-aminopenicillanic acid) of a noncrystalline solid product is obtained. IR spectrum in methylene chloride: 3400, 3000, 1805, 1760, 1720 and 1500 cm$^{-1}$.

(c) Preparation of (2R) methyl 2-((3S,4S)-4-acetoxy-3-benzyloxycarbonylaminoazetidin-2-on-1-yl)-3-methylbut-3-enoate)

A mixture containing 11.4 g (30 mmol) (R) methyl 6-benzyloxycarbonylaminopenicillanate-β-sulfoxide, 15 ml of trimethyl phosphite and 5.1 ml of acetic acid in 600 ml of benzene is refluxed for 40 hours in a nitrogen atmosphere. The mixture is cooled and washed with 200 ml of saturated sodium bicarbonate solution. The organic layer is dried over sodium sulfate and the solvent removed in vacuo. Chromatography of the residue on 450 g of silica gel using a 7:1 mixture of toluene and ethyl acetate (15 fractions, and a 3:1 mixture of toluene and ethyl acetate (6 fractions, 500 ml each) affords 7.3 g (63%) pure product as a noncrystalline solid (title compound). IR spectrum in methylene chloride: 3400, 3000, 1795, 1740, and 1510 cm$^{-1}$.

(d) Preparation of methyl 2-((3S,4S)-4-acetoxy-3-benzyloxycarbonylaminoazetidin-2-on-1-yl)-3-methylbut-2-enoate A mixture containing 6.7 g (17.2 mmol) of (2R) methyl 2-((3S,4S)-4-acetoxy-3-benzyloxycarbonylaminoazetidine-2-on-1-yl)-3-methylbut-3-enoate and 1.8 ml of triethylamine in 180 ml of methylene chloride is refluxed for 60 minutes in a nitrogen atmosphere. After cooling of the solution it is washed subsequently with 100 ml aqueous 1N hydrogen chloride solution and 100 ml of saturated sodium chloride solution. The organic layer is dried over sodium sulfate, filtered and evaporated in vacuo. In this way, 6.6 g (98%) of title compound as a pure, noncrystalline solid is obtained. IR spectrum in methylene chloride: 3400, 3000, 1790, 1730, 1510 and 1210 cm$^{-1}$.

(e) Preparation of methyl ((3S,4S)-4-acetoxy-3-benzyloxycarbonylaminoazetidin-2-on-1-yl)-2-oxoacetate Into a solution of 970 mg (2.5 mmol) methyl 2-((3S,4S)-4-acetoxy-3-benzyloxycarbonylaminoazetidin-2-on-1-yl)-3-methylbut-2-enoate in 40 ml of methanol, at −10° C., for 120 minutes a mixture of ozone and oxygen is introduced at a rate of 0.1 mmol per minute. The clear solution is diluted with 60 ml of methylene chloride and the mixture subsequently washed with 50 ml of aqueous sodium bisulfite solution (10%) and 100 ml of saturated sodium chloride solution. After drying of the organic layer over sodium sulfate, filtration and evaporation of the filtrate in vacuo 780 mg of a noncrystalline solid is obtained (86%) (title compound). IR spectrum in methylene chloride: 3400, 1835, 1755, 1720 and 1510 cm$^{-1}$.

This compound is used as starting material in example 16.

(f) Preparation of (3S,4S)-4-acetoxy-3-benzyloxycarbonylaminoazetidin-2-one

A mixture containing 2.34 g (6.43 mmol) methyl ((3S,4S)-4-acetoxy-3-benzyloxycarbonylaminoazetidin-2-on-1-yl)-2-oxoacetate and 5 ml of water in 250 ml of methanol is left at room temperature for 2 days. The mixture is evaporated in vacuo and the residue dried in high vacuo and recrystallized from methylene chloride-n-hexane. In this way, 1.33 g (74%) of title compound of melting point 110° to 113° C. is obtained. Chromatography of the mother liquors on 70 g of silica gel using a 3:1 mixture of toluene and ethyl acetate (20 fractions, 70 ml each) affords 300 mg (17%) pure crystalline product, additionally. IR spectrum in methylene chloride: 3500, 1800, 1745, 1730, 1510 and 1210 cm$^{-1}$.

This compound is used as starting material in example 13.

Further conversion of a compound obtained according to the process of the invention

EXAMPLE 20

Preparation of (S)-3-aminoazetidin-2-one

A solution of 22 mg (0.1 mmol) (S)-3-benzyloxycarbonylaminoazetidin-2-one (prepared according to example 16) in 4 ml of pure 95% ethanol is hydrogenated over 25 mg palladium on carbon (10%) for a period of 4 hours at ambient pressure. The reaction mixture is filtered and the filtrate evaporated in vacuo, leaving 9 mg (100%) of a crystalline residue (title compound) of a melting point 77° to 83° C. IR spectrum in methylene choride: 3420, 1760 and 1180 cm$^{-1}$.

I claim:

1. A process for the preparation of azetidin-2-ones of the formula I:

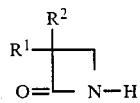   (I)

in which (i) $R^1$ and $R^2$ independent from each other are hydrogen, an alkyl group with 1 to 7 carbon atoms or an alkoxy group with 1 to 7 carbon atoms, or (ii) in which $R^1$ is an amino group or a protected amino group, and $R^2$ is hydrogen, an alkyl group with 1 to 7 carbon atoms or an alkoxy group with 1 to 7 atoms, provided that $R^1$ and $R^2$ cannot be an organic group linked via a carbonyl group to the ring carbon atom when one of the groups $R^1$ or $R^2$ is hydrogen, and characterized in that a 4-acyloxy-azetidin-2-one of the formula II:

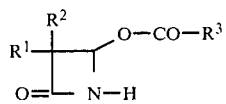   (II)

wherein $R^1$ and $R^2$ are as defined above and $R^3$ is selected from the group consisting of hydrogen and aliphatic, aromatic or arylaliphatic hydrocarbon radicals with up to 18 carbon atoms stable at the reaction conditions, is reacted with a complex hydride containing reactive hydride ions and of the formula:

$$A^o[XY_mH_n]_o$$

wherein A is selected from the group consisting of Li, K, Na, Ca, Mg, Zn and $(R^4)_4N$, in which $R^4$ is a lower alkyl group;

X = B or Al;

Y = H, an alkyl or alkoxy group with 1-7 carbon atoms, or a cyano group;

m = 1-3, n = 1-3, and m+n = 4; and o = valence of A.

2. The process of claim 1 wherein said complex hydride is selected from the group consisting of lithium borohydride, sodium borohydride, potassium borohydride, magnesium borohydride, calcium borohydride, zinc borohydride, sodium cyanoborohydride, and tetraalkylammonium borohydride containing up to 16 carbon atoms.

3. The process of claim 1 wherein said complex metal hydride is selected from the group consisting of lithium borohydride, sodium borohydride, potassium borohydride, zinc borohydride and tetraorganoammonium borohydride.

4. The process of either claim 1 or claim 2 wherein $R^1$ and $R^2$ independently from each other are hydrogen, an alkyl group with 1 to 7 carbon atoms or an alkoxy group with 1 to 7 carbon atoms.

5. The process of either claim 1 or claim 2 wherein $R^1$ is an amino group or a protected amino group, $R^2$ represents hydrogen, an alkyl group with 1 to 7 carbon atoms or an alkoxy group with 1 to 7 carbon atoms.

6. The process of claim 5, wherein one of the radicals $R^1$ and $R^2$ is hydrogen.

7. The process of claim 5 wherein $R^1$ is a protected amino group which has been protected by a hydrocarbonoxycarbonyl group or a hydrocarboncarbonyl group.

8. The process of claim 5, wherein $R^1$ is a protected amino group which has been protected by phenoxyacetyl, benzyloxycarbonyl or t-butyloxycarbonyl.

9. The process of claim 4 wherein one of the radicals $R^1$ and $R^2$ is hydrogen.

10. The process of either claim 1 or claim 3 wherein $R^3$ is an alkyl or aryl group with 1-7 carbon atoms.

* * * * *